US012655078B2

(12) United States Patent
Stone et al.

(10) Patent No.: US 12,655,078 B2
(45) Date of Patent: Jun. 16, 2026

(54) SELECTIVE PHOTOCATALYTIC REDUCTION OF ALKYNES TO ALKENES POWERED BY A COBALT-PORPHYRIN METAL-ORGANIC FRAMEWORKS

(71) Applicant: Northwestern University, Evanston, IL (US)

(72) Inventors: Aaron Edward Stone, Evanston, IL (US); Francesca Arcudi, Evanston, IL (US); Luka Dordevic, Evanston, IL (US); Emily Allyn Weiss, Evanston, IL (US); Joseph T. Hupp, Northfield, IL (US); Samuel Isaac Stupp, Evanston, IL (US)

(73) Assignee: Northwestern University, Evanston, IL (US)

( * ) Notice: Subject to any disclaimer, the term of this patent is extended or adjusted under 35 U.S.C. 154(b) by 258 days.

(21) Appl. No.: 18/391,358

(22) Filed: Dec. 20, 2023

(65) Prior Publication Data

US 2024/0208884 A1　　Jun. 27, 2024

Related U.S. Application Data

(60) Provisional application No. 63/434,354, filed on Dec. 21, 2022.

(51) Int. Cl.
C07C 5/09 (2006.01)
B01J 31/16 (2006.01)
(Continued)

(52) U.S. Cl.
CPC ............. C07C 5/09 (2013.01); B01J 31/1691 (2013.01); B01J 31/183 (2013.01); B01J 35/39 (2024.01);
(Continued)

(58) Field of Classification Search
CPC .... C07C 5/09; C07C 2531/22; B01J 31/1691; B01J 31/183; B01J 35/39;
(Continued)

(56) References Cited

U.S. PATENT DOCUMENTS 6,509,292 B1 　　1/2003　Blankenship et al.
10,329,217 B2 *　6/2019　Bunquin ................... C07C 5/05
(Continued)

FOREIGN PATENT DOCUMENTS

WO　　WO 2013/057244 A1　　4/2013

OTHER PUBLICATIONS

Organometallics 2019, 38, 3429-3435 (Year: 2019).*
(Continued)

*Primary Examiner* — Prem C Singh
*Assistant Examiner* — Francis C Campanell
(74) *Attorney, Agent, or Firm* — Bell & Manning, LLC

(57) ABSTRACT

Methods for the photocatalytic reduction of alkynes to alkenes with high conversion yields and selectivities using a heterogeneous system that incorporates a cobalt-porphyrin into a metal-organic framework (MOF) are provided. The cobalt-porphyrin-based MOFs carry out the photocatalytic reductions in the presence of a visible-light activated photosensitizer molecule and a sacrificial electron donor.

20 Claims, 19 Drawing Sheets

(51) Int. Cl.
  *B01J 31/18* (2006.01)
  *B01J 35/39* (2024.01)
(52) U.S. Cl.
  CPC .. *B01J 2231/645* (2013.01); *B01J 2531/0216*
    (2013.01); *B01J 2531/48* (2013.01); *B01J*
    *2531/821* (2013.01); *B01J 2531/845* (2013.01)
(58) Field of Classification Search
  CPC .......... B01J 2231/645; B01J 2531/0216; B01J
      2531/48; B01J 2531/821; B01J 2531/845
  USPC ........................................................ 585/274
  See application file for complete search history.

(56) References Cited

U.S. PATENT DOCUMENTS

2018/0296569 A1* 10/2018 Szade ................... A61K 31/555
2024/0208885 A1* 6/2024 Arcudi ................... B01J 31/183

OTHER PUBLICATIONS

Reuben B. Leveson-Gower et al. "Unlocking Iminium Catalysis in Artificial Enzymes to Create a Friedel-Crafts Alkylase," *ACS Catalysis* 2021, 11, 6763-6770.
Yanan Liu et al., "Adsorbate-Induced Structural Evolution of PD Catalyst for Selective Hydrogenation of Acetylene," *ACS Catal.* 2020, 10, 15048-15059.
Shiqi Zhou et al., "Pd Single-Atom Catalysts on Nitrogen-Doped Graphene for the Highly Selective Photothermal Hydrogenation of Acetylene to Ethylene," *Advanced Materials* 2019, 31, 1900509 (1 of 7).
Francesca Arcudi et al., "Selective visible-light photocatalysis of acetylene to ethylene using a cobalt molecular catalyst and water as a proton source," *Nature Chemistry* Sep. 2022, vol. 14, 1007-1012. https://doi.org/10.1038/s41557-022-00966-5.
Jun Bu et al., "Selective electrocatalytic semihydrogenation of acetylene impurities for the production of polymer-grade ethylene," *Nature Catalysis* Jul. 2021, vol. 4, 557-564.
Jingyu Cai et al., "MOF derived C/Co@C with a "one-way-valve"-like graphitic carbon layer for selective semi-hydrogenation of aromatic alkynes," *Carbon* (2020), 160, 64-70.
Luning Chen et al., "Controlled Encapsulation of Flower-like Rh—Ni Alloys with MOFs via Tunable Template Dealloying for Enhanced Selective Hydrogenation of Alkyne," *ACS Appl. Mater. Interfaces* 2016, 8, 31059-31066.
Kai-Jie Chen et al., "Synergistic sorbent separation for one-step ethylene purification from a four-component mixture," *Science* (Oct. 11, 2019), 366, 241-246.
Xili Cui et al., "Pore chemistry and size control in hybrid porous materials for acetylene capture from ethylene," *Science* (Jul. 2016), vol. 353, Issue 6295, 141-144.
Sai Puneet Desai et al., "Well-Defined Rhodium-Gallium Catalytic Sites in a Metal-Organic Framework: Promoter-Controlled Selectivity in Alkyne Semihydrogenation to E-Alkenes," *J. Am. Chem. Soc.* (2018), 140, 15309-15318.
Sai Puneet Desai et al., "Mechanistic Study on the Origin of the Trans Selectivity in Alkyne Semihydrogenation by a Heterobimetallic Rhodium-Gallium Catalyst in a Metal-Organic Framework," *Organometallics* (2019), 38, 3466-3473.
Ming-Jie et al., "Creation of Redox-Active PdSx Nanoparticles Inside the Defect Pores of MOF UiO-66 with Unique Semihydrogenation Catalytic Properties," *Adv. Funct. Mater.* 2020, 30, 1908519 (1 of 9).
Dawei Feng et al., "Zirconium-Metalloporphyrin PCN-222: Mesoporous Metal-Organic Frameworks with Ultrahigh Stability as Biomimetic Catalysts**," *Angew. Chem. Int. Ed.* 2012, 51, 10307-10310.
Ryan A. Hackler et al., "Isomerization and Selective Hydrogenation of Propyne: Screening of Metal-Organic Frameworks Modified by Atomic Layer Deposition," *J. Am. Chem. Soc.* 2020, 142, 20380-20389.

Tong-Liang Hu et al., "Microporous metal-organic framework with dual functionalities for highly efficient removal of acetylene from ethylene/acetylene mixtures," *Nature Communications* (Jun. 4, 2015), 6:7328, 1-9.
Debiao Huo et al. "Ruthenium Complex-Incorporated Two-Dimensional Metal-Organic Frameworks for Cocatalyst-Free Photocatalytic Proton Reduction from Water," *Inorg. Chem.* 2020, 59, 2379-2386.
Yuchao Chai et al., "Acetylene-Selective Hydrogenation Catalyzed by Cationic Nickel Confined in Zeolite," *J. Am. Chem. Soc.* 2019, 141, 9920-9927.
Long Jiao et al., "Nanocasting SiO2 into metal-organic frameworks imparts dual protection to high-loading Fe single-atom electrocatalysts," *Nature Communications* 2020, 11:2831, 1-7. https://doi.org/10.1038/s41467-020-16715-6.
Abebu A. Kassie et al., "Catalytic Activity of a Zr MOF Containing POCOP-Pd Pincer Complexes," *Organometallics* 2020, 39, 2214-2221.
Libo Li et al., "Efficient separation of ethylene from acetylene/ethylene mixtures by a flexible-robust metal-organic framework†," *J. Mater. Chem. A.* (Sep. 28, 2017), vol. 5, No. 36, 18899-19502.
Zekai Lin et al., "Highly Efficient Cooperative Catalysis by CoIII(Porphyrin) Pairs in Interpenetrating Metal-Organic Frameworks," *Angew. Chem. Int. Ed.* 2016, 55, 13739-13743.
Yiming Niu et al., "Manipulating interstitial carbon atoms in the nickel octahedral site for highly efficient hydrogenation of alkyne," *Nature Communications* (2020), 11:3324, 1-9. https://doi.org/10.1038/s41467-020-17188-3.
Davide Albani et al., "Selective ensembles in supported palladium sulfide nanoparticles for alkyne semi-hydrogenation," *Nature Communications* 2018, 9:2634, 1-11. DOI: 10.1038/s41467-018-05052-4.
Chun Wong Aaron Chan et al., "Interstitial modification of palladium nanoparticles with boron atoms as a green catalyst for selective hydrogenation," *Nature Communications* (Dec. 19, 2014), 5:5787, 1-10.
M. Armbruster et al., "Al13Fe4 as a low-cost alternative for palladium in heterogeneous hydrogenation," *Nature Materials* (Aug. 2012), vol. 11, 690-693.
Dayne F. Swearer et al., "Heterometallic antenna-reactor complexes for photocatalysis," *PNAS* (Aug. 9, 2016), vol. 113, No. 32, 8916-8920.
Louis R. Redfern et al., "Enhancing Four-Carbon Olefin Production from Acetylene over Copper Nanoparticles in Metal-Organic Frameworks," *ACS Appl. Mater. Interfaces* 2020, 12, 312496-31502.
Songhyun Lee et al., "Dynamic metal-polymer interaction for the design of chemoselective and long-lived hydrogenation catalysts," *Sci. Adv.* (Jul. 8, 2020), 6, eabb7369 (1 of 10).
Kunlun Ding et al., "A general synthesis approach for supported bimetallic nanoparticles via surface inorganometallic chemistry," *Science* (Nov. 2, 2018), vol. 362, Issue 6414, 560-564.
Detre Teschner et al., "The Roles of Subsurface Carbon and Hydrogen in Palladium-Catalyzed Alkyne Hydrogenation," *Science* (Apr. 4, 2008), vol. 320, 86-89.
Jin Shen et al., "Simultaneous interlayer and intralayer space control in two-dimensional metal-organic frameworks for acetylene/ethylene separation," *Nature Communications* (2020), 11:6259, 1-10.
Run Shi et al., "Room-temperature electrochemical acetylene reduction to ethylene with high conversion and selectivity," *Nature Catalysis* (Jul. 2021), vol. 4, 565-574.
Takashi Toyao et al., "Development of a Ru complex-incorporated MOF photocatalyst for hydrogen production under visible-light irradiation†," *Chem. Commun.*, 2014, 50, 6779.
Yutong Wang et al., "One-step Ethylene Purification from an Acetylene/Ethylene/Ethane Ternary Mixture by Cyclopentadiene Cobalt-Functionalized Metal-Organic Frameworks," *Angew. Chem. Int. Ed.* 2021, 60, 11350-11358.
Sheng-Chang Xiang et al., "Rationally tuned micropores within enantiopure metal-organic frameworks for highly selective separation of acetylene and ethylene," *Nature Communications* (Feb. 22, 2011), 2:204, 1-7.

(56) References Cited

OTHER PUBLICATIONS

Tianhua Zhou et al., "Post-synthesis modification of a metal-organic framework to construct a bifunctional photocatalyst for hydrogen productiont†," *Energy Environ. Sci.*, 2013, 6, 3229-3234.

Baoyong Zhu et al., "Pore Engineering for One-Step Ethylene Purification from a Three-Component Hydrocarbon Mixture," *J. Am. Chem. Soc.* 2021, 143, 1485-1492.

Guanglong Ding et al. "Porphyrin-Based Metal-Organic Frameworks for Neuromorphic Electronics," *Small Structures* 2023, 4, 2200150 (1 of 23).

Sreehar Surendran Rajasree et al.,"Physical properties of porphyrin-based crystalline metal-organic-frameworks," *Communications Chemistry* 2021, 4:47.

Yann Pellegrin et al., "Sacrificial electron donor reagents for solar fuel production," *C.R. Chimie* 20 (2017), 283-295.

Johannes Karges et al., "Rationally designed ruthenium complexes for 1- and 2-photon photodynamic therapy," *Nature Communications* (2020), 11:3262.

Sergio Carrasco et al., "Hf/porphyrin-based metal-organic framework PCN-224 for CO2 cycloaddition with epoxides," *Materials Today Advances* (2023), 19, 100390.

Poster Presentation at International Conference on Metal-Organic Frameworks and Open Frameworks Compounds, Sep. 4, 2022.

Sergio Carrasco et al., Fast and Robust Synthesis of Metalated PCN-222 and Their Catalytic Performance in Cycloaddition Reactions with CO2, *Organometallics* 2019, 38, 3429-3435.

Book of Abstracts: "International Conference on Metal-Organic Frameworks and Open Frameworks Compounds," International Congress Centre Dresden—Germany, Sep. 4-7, 2022, 1-3.

Hosein Ghasempour et al., "Metal-Organic Frameworks Based on Multicarboxylate Linkers," Version of Record: https://www.sciencedirect.com/science/article/pii/S001085452030638X, 2020, 1-46.

Li, L.; Lin, R.-B.; Krishna, R.; Li, H ; Xiang, S.; Wu, H.; Li, J.; Zhou, W.; Chen, B., "Ethane/ethylene separation in a metal-organic framework with iron-peroxo sites," *Science* 2018, 362 (6413), 443-446.

\* cited by examiner

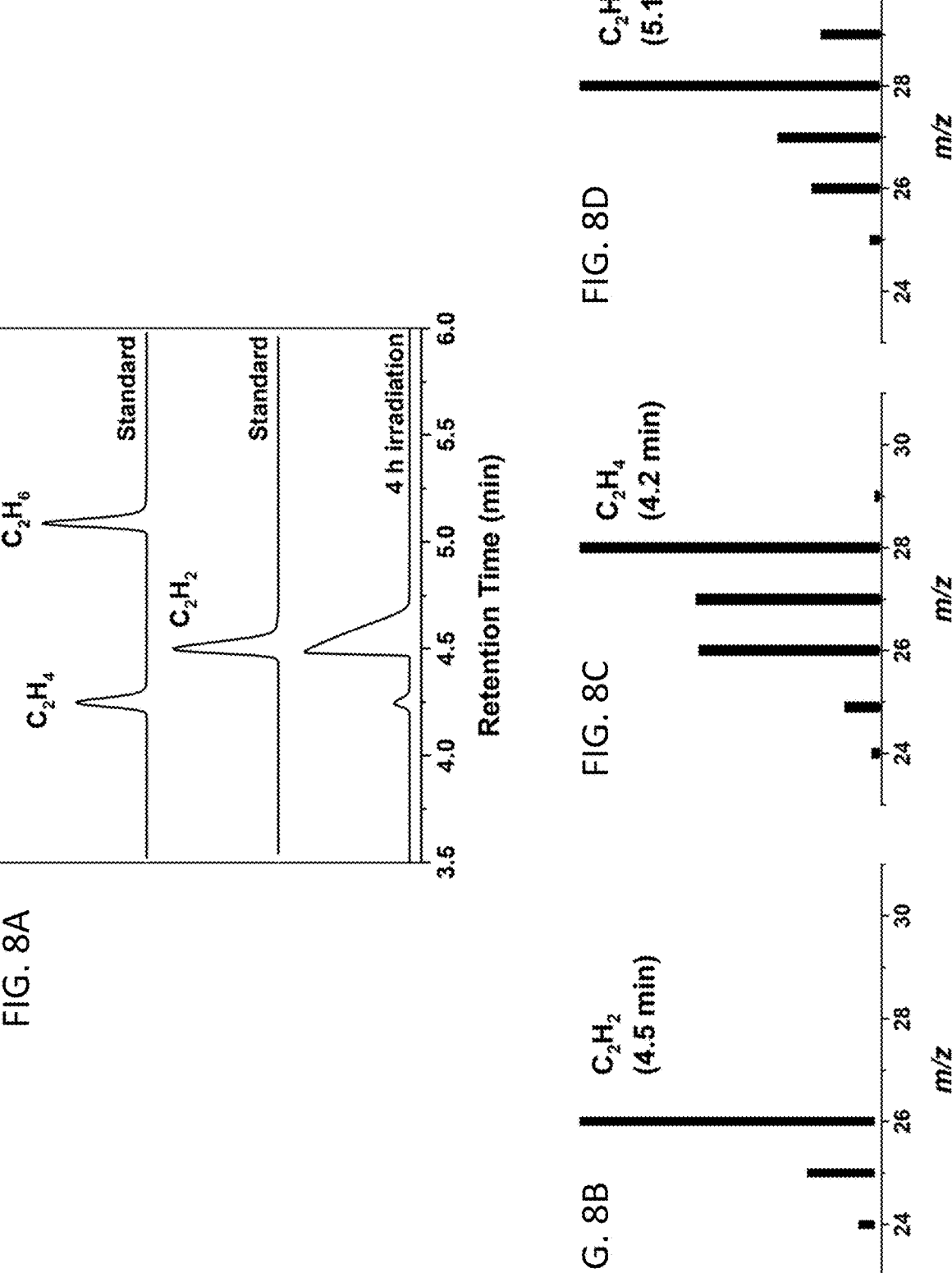

SELECTIVE PHOTOCATALYTIC REDUCTION OF ALKYNES TO ALKENES POWERED BY A COBALT-PORPHYRIN METAL-ORGANIC FRAMEWORKS

CROSS-REFERENCE TO RELATED APPLICATIONS

The present application claims priority to U.S. provisional patent application No. 63/434,354 that was filed Dec. 21, 2022, the entire contents of which are incorporated herein by reference.

REFERENCE TO GOVERNMENT RIGHTS

This invention was made with government support under DE-SC002-11690001 and DE-FG02-87ER13808 awarded by the Department of Energy. The government has certain rights in the invention.

BACKGROUND

Ethylene ($C_2H_4$), one of the world's most important commodity chemicals, is an intermediate in 50-60% of all plastics. (Geyer, R. et al., *Science Advances* 2017, 3 (7), e1700782.) Of the nearly 200 million tons of ethylene produced annually, the vast majority is derived from the steam cracking of petroleum. (Sholl, D. S. et al., *Nature* 2016, 532 (7600), 435-437.) Steam cracking unavoidably introduces impurities into the ethylene gas stream, the most pernicious of which (from the standpoint of plastics production) is acetylene. (Studt, F. et al., *Science* 2008, 320 (5881), 1320-1322.) Crude ethylene streams typically contain ~0.5-2 vol. % acetylene, which is a potent poison for the Ziegler-Natta catalysts used for ethylene polymerization. (Borodziński, A. et al., *Catalysis Reviews* 2006, 48 (2), 91-144.) It is therefore necessary to reduce the acetylene concentration to a few ppm to obtain polymer-grade ethylene prior to plastics production. (Studt, F., 2008.)

The current state-of-the-art technology for purifying crude ethylene streams is the thermocatalytic hydrogenation of acetylene to ethylene (FIG. 1A). While this process is currently deployed on an industrial scale, it suffers from several drawbacks including: (i) the need for high temperatures and high pressures, which necessitates a large energy input; (ii) the need for $H_2$ gas as co-feed (primarily derived from the steam reformation of methane), usually in excess; and (iii) the use of precious metal Pd as catalyst, which contributes to high costs ($10,000 per kg Pd). (Borodziński, A. et al., 2006; Studt, F., 2008.) Following the reaction, the excess $H_2$ must be separated from the reaction mixture to avoid possible thermal runaway processes. (Borodziński, A. et al., 2006.) The use of Pd also introduces the potential for over-hydrogenation to ethane, an inherent constraint on the precious-metal-based systems that employ $H_2$ as the hydrogen source, and limits the selectivity to 85% at >90% conversion at 200° C. (Studt, F., 2008; Borodziński, A. et al., 2006; Armbrüster, M. et al, *Nat. Mater.* 2012, 11 (8), 690-693.) All these issues make the thermocatalytic process unsustainable due to cost and environmental impact.

An improved strategy for the purification of ethylene would eliminate the precious-metal catalysts, $H_2$ co-feed, and high temperatures and pressures of the thermocatalytic route, while simultaneously improving activity and selectivity. Recently, several such alternative methods have been pursued in academic laboratories. For instance, the physical separation of acetylene from ethylene using sorbent materials avoids the intense energy utilization of the thermocatalytic approach. (Chen, K.-J. et al., *Science* 2019, 366 (6462), 241-246; Li, L. et al., *Science* 2018, 362 (6413), 443-446.) The separated acetylene is wasted, however, rather than being converted into valuable ethylene. Electrochemistry and photochemistry provide milder alternatives for the conversion of acetylene to ethylene. Two reports demonstrated that electrocatalytic systems based on copper catalysts achieve near 100% conversion of acetylene to ethylene in the presence of an excess of ethylene with high selectivity for ethylene (90.1%-97%). (Bu, J. et al., *Nature Catalysis* 2021, 4 (7), 557-564; Shi, R. et al., *Nature Catalysis* 2021, 4 (7), 565-574.

In a homogenous system, cobalt porphyrins ([meso-tetra (4-sulfonatophenyl)porphyrinato]-cobalt(III), Co-TPPS and [meso-tetra(4-carboxyphenyl) porphyrinato]-cobalt(II), Co-TCPP), in the presence of photosenstizer (PS) and sacrificial donor are effective photocatalysts for the semihydrogenation of acetylene to ethylene. (Arcudi, F. et al., *Nat Chem* 2022, 14 (9), 1007-1012.)

SUMMARY

Methods for the photocatalytic reduction of alkynes to alkenes using a heterogeneous system that incorporates a cobalt-porphyrin into a metal-organic framework (MOF) are provided. One embodiment of a method for the photocatalytic reduction of an alkyne to an alkene includes the steps of: exposing the alkyne to a solution comprising: a metal-organic framework comprising inorganic metal ions or clusters connected by polytopic organic linkers, the polytopic organic linkers comprising cobalt-porphyrin groups; a photosensitizer; and a sacrificial donor; and irradiating the photosensitizer to visible radiation to induce the photocatalytic reduction of the alkyne to the alkene.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 4A shows a plot of acetylene conversion (%), residual acetylene (ppm), and ethylene selectivity vs. ethane (%) as a function of irradiation time. FIG. 4B shows gas chromatograms (the elution order is $C_2H_4$, $C_2H_6$, $C_2H_2$) detected with flame ion detection before and after irradiation (450 nm) for 87 h. The inset is a magnified view of the acetylene peak in the chromatogram before and after illumination.

FIG. 6A shows a Calibration curve for $C_2H_4$ with the corresponding coefficient of linear correlation ($R^2$). FIG. 6B shows a calibration curve for $C_2H_6$ with the corresponding coefficient of linear correlation ($R^2$).

FIG. 7A shows a calibration curve for $C_2H_4$ with the corresponding coefficient of linear correlation ($R^2$). FIG. 7B shows a calibration curve for $C_2H_6$ with the corresponding coefficient of linear correlation ($R^2$).

FIGS. 8A-8D show typical GC-MS chromatograms and mass spectra observed for the photoreduction of acetylene. FIG. 8A shows gas chromatograms of the $C_2H_4$/$C_2H_6$ standard. $C_2H_2$ standard, and the $C_2H_2$ (99.5 vol. %)-purged acetonitrile solution containing 2.5 mM $Ru(bpy)_3^{2+}$, 0.8 mg Co-PCN-222, and 1.25 M TEOA after irradiation with 450 nm light (140 mW·cm$^{-2}$) for 4 hours. FIG. 8B shows a mass spectrum of $C_2H_2$. FIG. 8C shows a mass spectrum of $C_2H_4$. FIG. 8D shows a mass spectrum of $C_2H_6$.

(FIG. 11C) Optimization of $C_2H_4$ selectivity vs. $C_2H_6$ and $H_2$ (mmol g$^{-1}$ Co) produced through variation of amount of MOF (mg). The samples contain 2.5 mM $Ru(bpy)_3^{2+}$ and 1.25 M TEOA in acetonitrile under $C_2H_2$ ($\geq$99.5 vol. %) and were irradiated for 4 h. Error bars represent the standard deviations for at least three separate experiments.

FIG. 16A shows gas chromatograms of $C_3H_6$/$C_3H_8$ standard and a He-purged acetonitrile solution injected with 350 μL $C_3H_4$ ($\geq$99 vol. %) containing 2.5 mM $Ru(bpy)_3^{2+}$, 0.8 mg Co-PCN-222, and 1.25 M TEOA before and after irradiation at 450 nm (140 mW·cm$^{-2}$) for 20 hours. FIG. 16B shows mass spectrum of $C_3H_8$. FIG. 16C shows mass spectrum of $C_3H_4$. FIG. 16D shows mass spectrum of $C_3H_6$.

DETAILED DESCRIPTION

Methods for the photocatalytic reduction of alkynes to alkenes using a heterogeneous system that incorporates a cobalt-porphyrin into a metal-organic framework (MOF) are provided. Alkynes that can be photocatalytically reduced using the methods described herein include acetylene and propyne, which are reduced to ethylene and propylene, respectively. The methods described herein combine the high activity and selectivity of homogeneous system with the ease of separability, recyclability, and robustness of a heterogeneous system.

In some embodiments of the methods, the photocatalyst is the metal-organic framework Co-PCN-222 and the photosensitizer is tris(2,2'-bipyridyl)dichlororuthenium(II) hexahydrate.

The methods can be used for the production of polymer-grade gas streams and have applications in, for example, the purification of alkene streams for the upgrade of low weight fractions from stream crackers; the production of intermediates in the manufacture of fine chemicals; purifying crude ethylene gas streams to produce polymer-grade ethylene; and purifying crude propylene streams to produce polymer-grade propylene. The ability to photocatalytically purify acetylene from industrial ethylene streams to produce polymer-grade ethylene is a significant accomplishment, as this is one of the most important and energy-demanding reactions being used today.

The MOF-based photocatalytic reductions are robust and avoid the use of noble metal catalysts (reducing cost and the environmental impact of extracting such metals), high temperatures and pressures (which generate significant greenhouse gas emissions), and a $H_2$ gas feed (the production of which contributes significantly to greenhouse gas emissions and is potentially explosive in an industrial setting), all while achieving significantly higher selectivity than the current industry standard. Additionally, the heterogeneous nature of the MOF-based catalyst leads to an increased longevity compared to a homogeneous system, and allows for easy isolation of the catalyst from the reaction mixture.

The photocatalytic reductions can be activated using visible radiation, which may be provided by solar radiation. The ability to directly utilize abundant, sustainable solar irradiation as the energy input to perform these important chemical transformations is an attractive alternative to the state-of-the-art industrial reaction.

MOFs are a class of porous, crystalline, multi-dimensional nanomaterials composed of inorganic metal ions or clusters (nodes) connected by polytopic organic molecules (linkers). (Howarth, A. J. et al., *Nat. Rev. Mater.* 2016, 1 (3); Howarth, A. J. et al., *Chem. Mater.* 2017, 29 (1), 26-39.) The long-range order of MOFs makes it possible to engineer the same microenvironment around all catalyst species, to achieve "single-site catalysis."

Figure 1A:
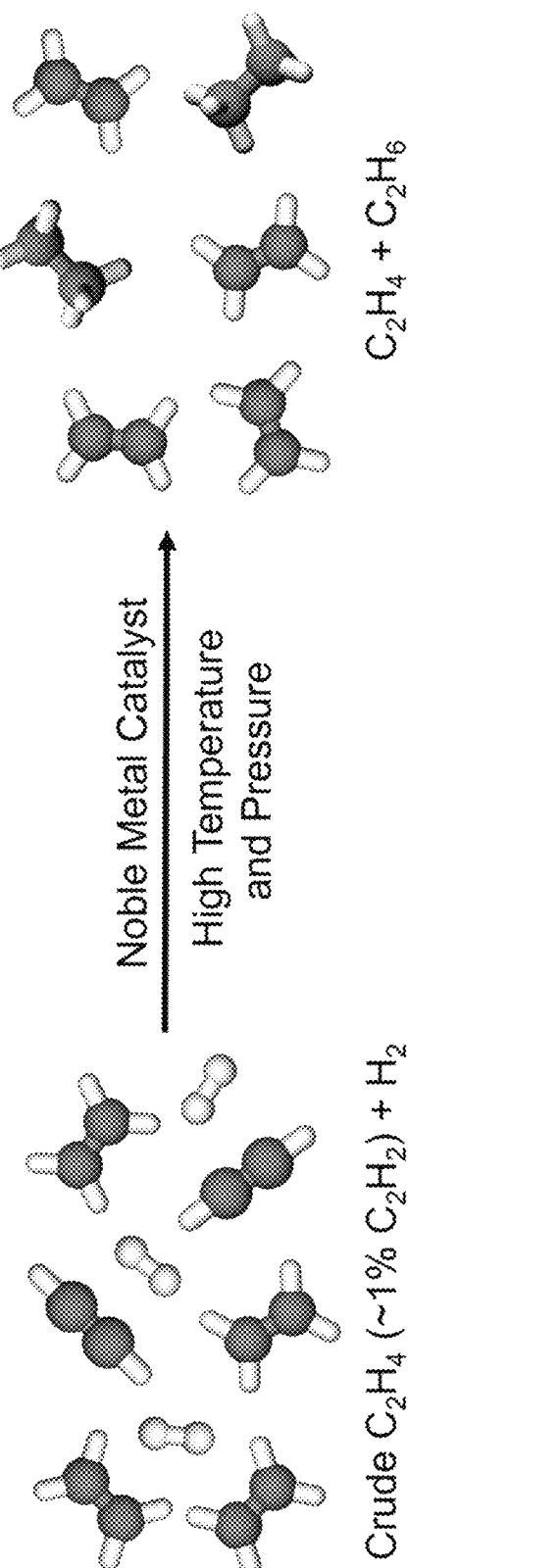
FIG. 1A shows current state-of-the-art technology for acetylene to ethylene conversion, which involves hydrogenation of acetylene using a noble metal catalyst and $H_2$ at high temperatures.
Figure 1B:
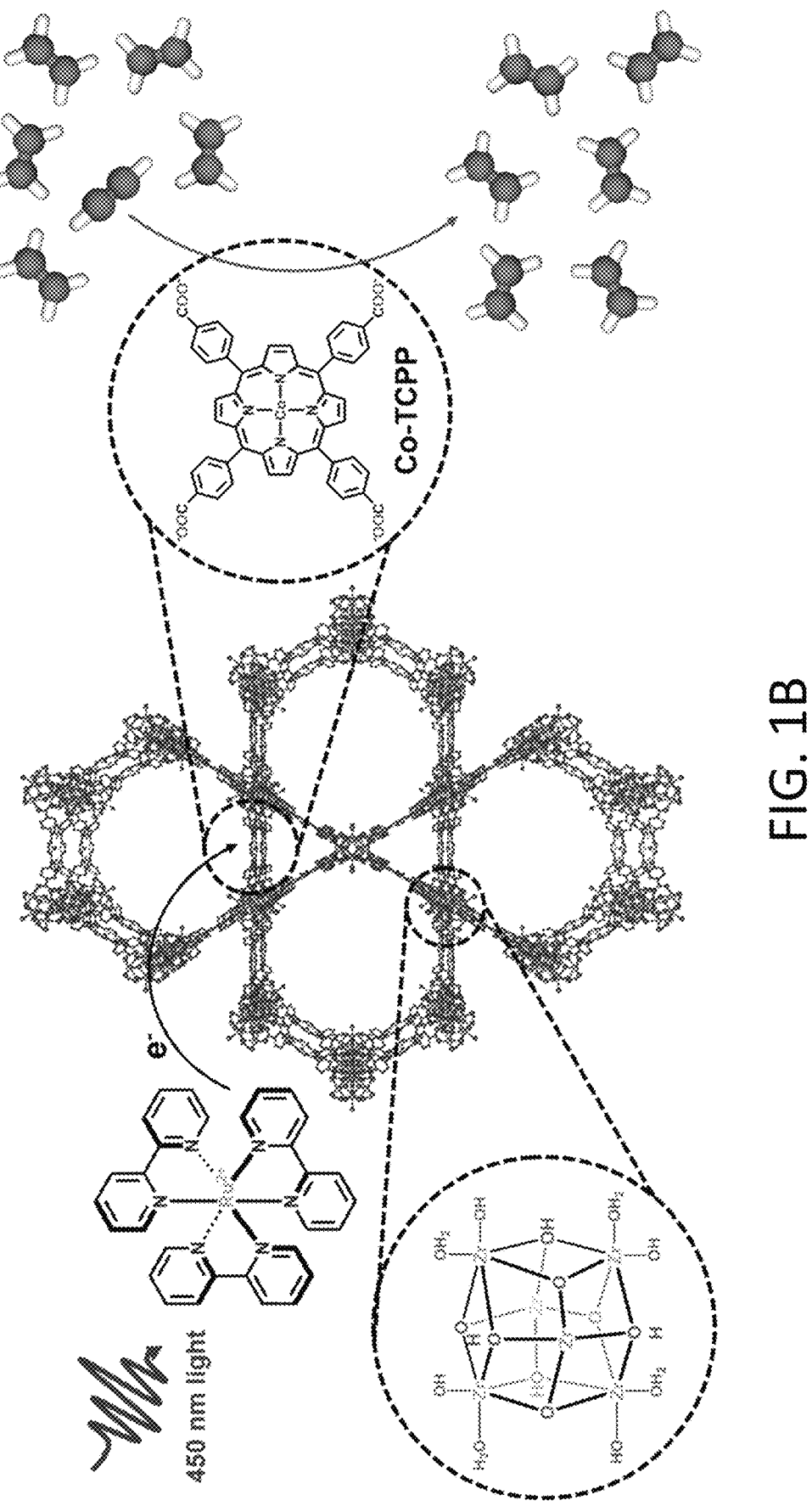
FIG. 1B shows the MOF-based photocatalytic scheme laid out in this work, in which $Ru(bpy)_3^{2+}$ is used to photosensitize earth-abundant Co catalyst supported by the Zr-based PCN-222 framework, which reduces acetylene to ethylene photocatalytically at room temperature and with high conversion and selectivity.

The cobalt-porphyrin-based MOFs used in the photocatalytic reduction of alkynes incorporate porphyrin groups that are complexed with cobalt (Co) ions into their linkers. The porphyrin groups may be incorporated into the linkers as tetrakis(4-carboxyphenyl)porphyrin (TCPP) groups, but other phophyrin group-containing linkers can also be used. The cobalt-porphyrin-based MOFs may be zirconium (Zr) MOFs—that is, MOFs in which the metal ions or clusters of the nodes are Zr, such as Co—(Zr)PCN-222. The structure of Co—(Zr)PCN-222 is shown in FIG. 1B. However, cobalt-porphyrin-based MOFs having other metals in their nodes can also be used. These include analogues of Co—(Zr)PCN-222 in which Zr is replaced with another metal. Other metals include hafnium (Hf), iron (Fe), aluminum (Al), and chromium (Cr).

Figures 5A, 5B:
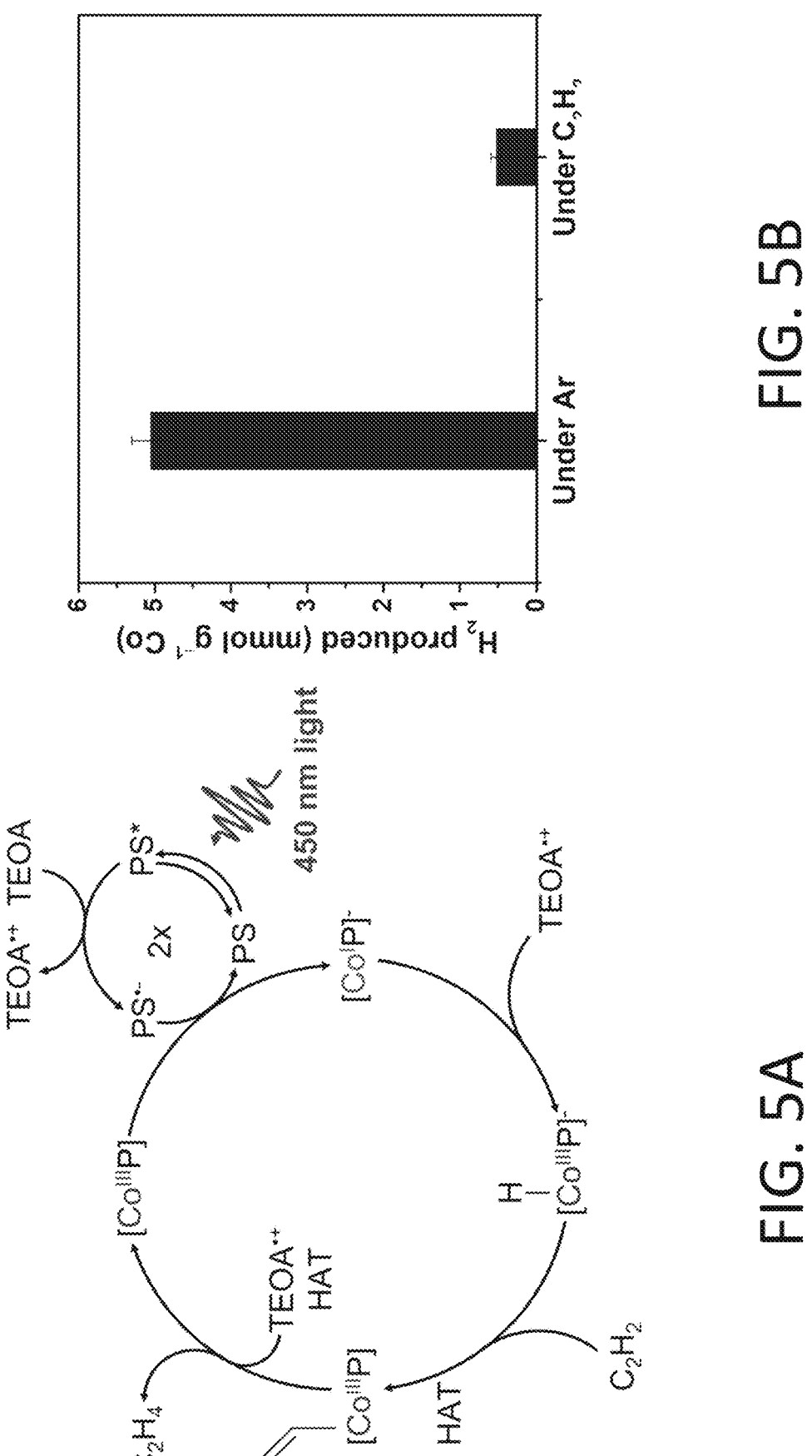
FIG. 5A shows proposed catalytic mechanism for the photocatalytic reduction of acetylene to ethylene using Co-PCN-222.
FIG. 5B shows $H_2$ evolution by the $Ru(bpy)_3^{2+}$/Co-PCN-222 system under acetylene or Ar.

The photocatalytic reductions are carried out by the cobalt-porphyrin-based MOFs in the presence of a photosensitizer and a sacrificial donor. The mechanism of the photocatalytic reduction of the alkynes to their respective alkenes is also shown in FIG. 5A. The photocycle for the photosensitizer (PS) and the sacrificial (electron) donor (SD) is shown in the upper right of the figure. During this photocycle, the PS is promoted to an excited state (PS*) by the absorption of the visible radiation. The excited PS undergoes a redox reaction with the SD, whereby the SD donates an electron to PS*. As a result, the SD is oxidized $(SD^{\cdot+})$ and PS* is reduced $(PS^{\cdot-})$. This quenching of PS* by the SD is referred to as reductive quenching. The reduced PS can then undergo a redox reaction with the cobalt-porphyrin group of a MOF, whereby the photosensitizer is oxidized (PS) and the cobalt is reduced. This photocycle for a generic PS and the SD triethanolamine (TEAO) is shown in FIG. 5A.

Generically, the mechanism is as follows: following photoexcitation of the PS and the subsequent reductive quenching of the photoexcited PS by the SD, the resulting oxidized PS reduces the cobalt in the cobalt-porphyrin group of the MOF from Co(III) to Co(I). The Co(I) then accepts a proton from the oxidized SD, to form a $Co^{III}$—H intermediate. The alkyne then inserts into the $Co^{III}$—H bond via hydrogen atom transfer. An additional proton and electron are supplied by $SD/SD^{\cdot+}$. Finally, the alkene is released, and the $Co^{III}$-linker is regenerated.

By way of illustration, using $Ru(bpy)_3^{2+}$ as an illustrative PS, TEAO as an illustrative SD, and Co—(Zr)PCN-222 as in illustrative MOF, the photocatalytic reduction of acetylene to ethylene is shown in FIG. 5A and has the following mechanism: following photoexcitation of Ru(bpy)$_3^{2+}$ and reductive quenching of $[Ru(bpy)_3^{2+}]^*$ by TEOA, the resulting $[Ru(bpy)_2(bpy)^{\cdot-}]^+$ reduces $Co^{III}$-TCPP in Co-PCN-222 twice to form $Co^I$-TCPP. $Co^I$-TCPP accepts a proton from the oxidized $TEOA^{\cdot+}$ to form a $Co^{III}$—H intermediate. $C_2H_2$ then inserts into the $Co^{III}$—H bond via hydrogen atom transfer (HAT). An additional proton and electron are supplied by $TEOA/TEOA^{\cdot+}$. Finally, $C_2H_4$ is released, and $Co^{III}$-TCPP is regenerated.

Any photosensitizer capable of participating in the above-described PS/SD photocycle upon excitation by visible radiation can be used. (Visible radiation includes radiation having wavelengths in the range from about 400 nm to about 700 nm.) The visible radiation may be provided by solar radiation. The photosensitizer may be a rubidium complex, such as a rubidium polypyridine complex. One example of a rubidium polypyridine complex is tris(bipyridine)ruthenium(II) $(Ru(bpy)_3^{2+}$.

The sacrificial donor may be any molecule capable of participating in the above-described PS/SD photocycle. The sacrificial donor may be, for example, a tertiary aliphatic amine, such as triethylamine, TEAO, or ethylenediaminetetraacetic acid (EDTA).

The solution containing the alkyne, photosensitizer, and sacrificial donor may be an aqueous solution or a non-aqueous solution, and can be selected based on the solubilities of the alkyne, photosensitizer, and sacrificial donor. Acetonitrile (ACN) is one example of a solvent that can be used. Others suitable solvents include dimethylformamide (DMF). These organic solvents can be used alone or in mixtures with other organic solvents and/or in mixtures with water.

Using the cobalt-porphorin-based MOFs for the photocatalytic reduction of alkynes to alkenes produces the alkenes with a high conversion and is highly selective for alkynes over alkenes. The photocatalytic reductions convert alkynes, such as acetylene and propyne, to alkenes, such as ethylene and propylene, with at least an 80 percent (based on moles), at least 90 percent, at least 95 percent, at least 99 percent, at least 99.9 percent, and 100 percent conversion. The photocatalytic reductions selectively reduce alkynes, such as acetylene and propyne, over alkenes, such as ethylene and propylene, with a selectivity of at least an 80 percent, at least 90 percent, at least 95 percent, at least 99 percent, at least 99.9 percent, and 100 percent selectivity. (Methods for determining conversions and selectivities are described in the Example.) Therefore, when the solution containing the MOF, the photosensitizer, and the sacrificial donor contacts an atmosphere comprising a mixture of alkyne and alkene gas molecules, all or nearly all the alkynes can be converted into alkenes without the reduction of the alkenes to their corresponding alkanes (i.e., without the production of the over-hydrogenation product). Notably, these high conversions and selectivities can be achieved under industrially relevant conditions.

The photocatalytic reductions can be carried out at or near room temperature (i.e., at temperatures in the range from 20° C. to 25° C.). However, higher and lower temperatures can be used. The photocatalytic reductions may be carried out in the presence of other gaseous chemical species. However, if other gaseous chemical species are present, it is desirable that these species do not interfere with the photocatalytic reductions ("inert" species). Thus, in some embodiments of the methods, the photocatalytic reduction is conducted in an atmosphere that includes only the alkynes or a mixture of alkynes and alkyenes and one or more inert gases, such as Ar.

Example

This Example illustrates the selective, photocatalytic semihydrogenation of acetylene to ethylene powered by visible light and at room temperature using Co-PCN-222. The semihydrogenation takes place in a photocatalytic mixture that comprises tris(2,2'-bipyridyl) dichlororuthenium (II) hexahydrate ($Ru(bpy)_3^{2+}$) as photosensitizer, triethanolamine (TEOA) as sacrificial donor, and acetonitrile (ACN) as solvent. We demonstrate that our MOF-based photocatalytic system converts acetylene to ethylene with >99.7% selectivity for ethylene and an overall production of 1.6 mol $g^{-1}$ Co in a pure acetylene feed, and retains its activity even after one week of irradiation, seven times as long as the homogeneous system. (Arcudi, F. et al., 2022.) Furthermore, in the presence of excess ethylene, i.e., the industrially relevant conditions, our system achieves near 100% conversion of acetylene to ethylene with >99.9% ethylene selectivity over ethane after 87 hours of irradiation. We investigated the mechanism of acetylene semihydrogenation and propose a catalytic route where two photoreductions of $Co^{III}$-TCPP yield the Co(I) active species that acts mainly as a base rather than a nucleophile, unlike the homogeneous system. The formation of a $Co^{III}$—H intermediate is followed by hydrogen atom transfer to acetylene, and a protonation step yields the product ethylene and restarts the cycle.

Results and Discussion

Synthesis and Characterization of Co-PCN-222.

The molecular catalysts were incorporated into MOFs as linkers to provide a heterogeneous photocatalyst for the semihydrogenation of acetylene by using Co-TCPP as the linker in the MOF Co-PCN-222. PCN-222 is a MOF composed of hexa-zirconium(IV) nodes and ([meso-tetra(4-carboxylatephenyl)porphine]. $TCPP^{4-}$) linkers (see FIG. 1B). (Feng, D. et al., Angew. Chem. Int. Ed. 2012, 51 (41), 10307-10310.) We chose Co-PCN-222 for its Zr(IV)-based nodes, as Zr-based MOFs typically exhibit excellent thermal and chemical stability, even under harsh conditions such as those we expected during photocatalysis; and its large mesoporous channels (3.7 nm in diameter), which facilitate mass transport during catalysis. The result is a robust photocatalyst with single-atom Co sites distributed homogeneously throughout the framework.

Figures 2A, 2B:
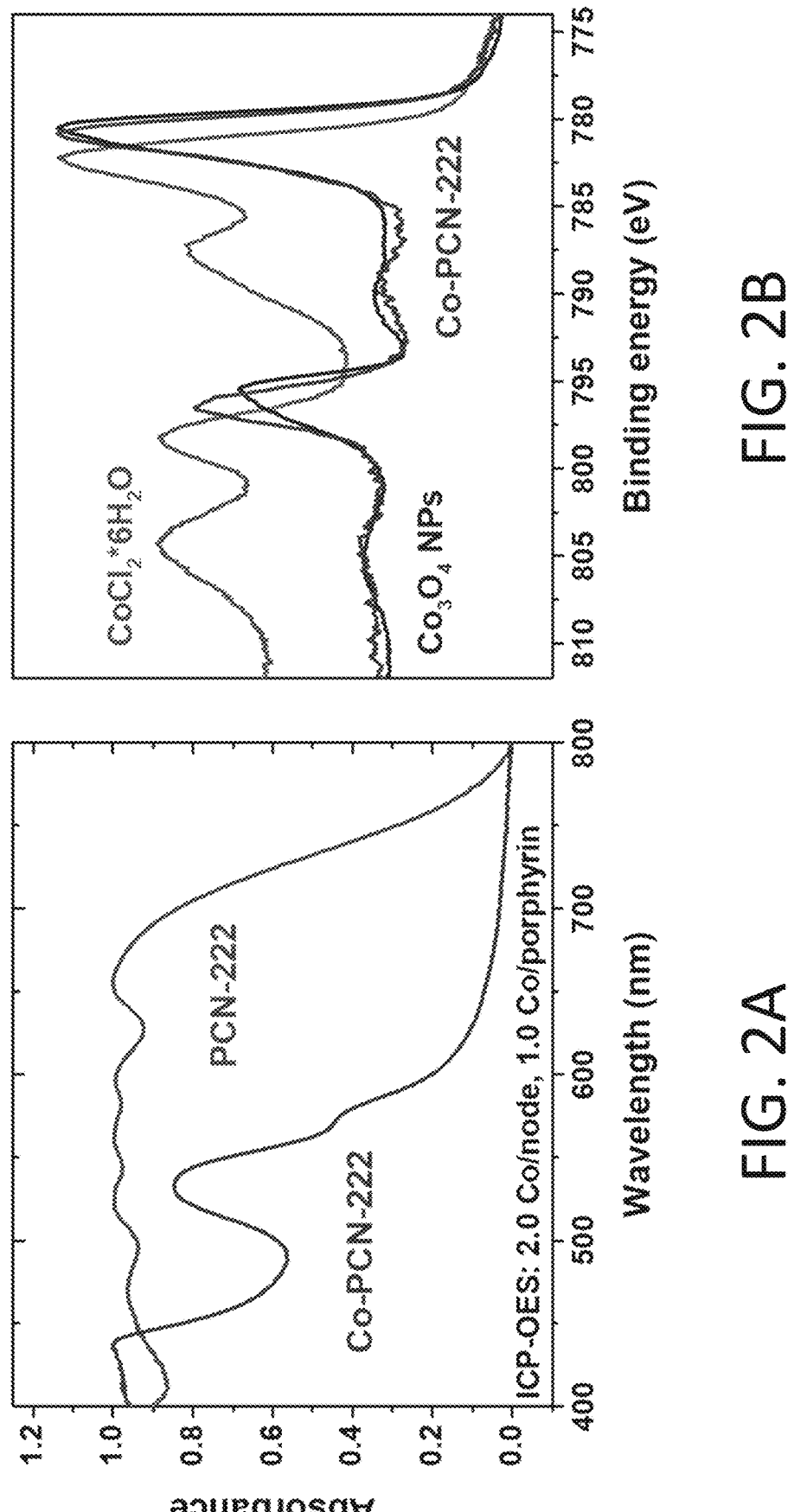
FIG. 2A shows DR-UV-Vis of PCN-222 (purple) and Co-PCN-222 (maroon).
FIG. 2B shows XPS spectrum of Co-PCN-222 and, for comparison, of $CoCl_2·6H_2O$ and $Co_3O_4$ nanoparticles.
Figure 2C:
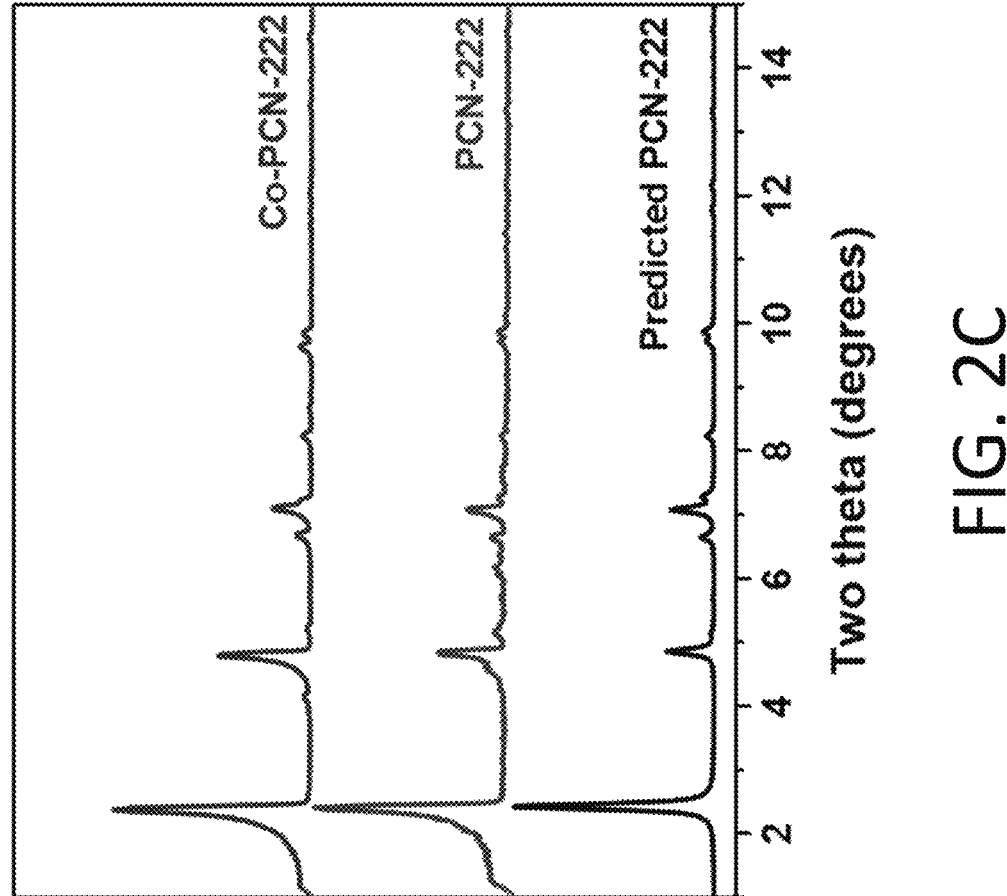
FIG. 2C shows predicted and experimental PXRD patterns of PCN-222 and the experimental PXRD pattern of Co-PCN-222.
Figures 2D, 2E:
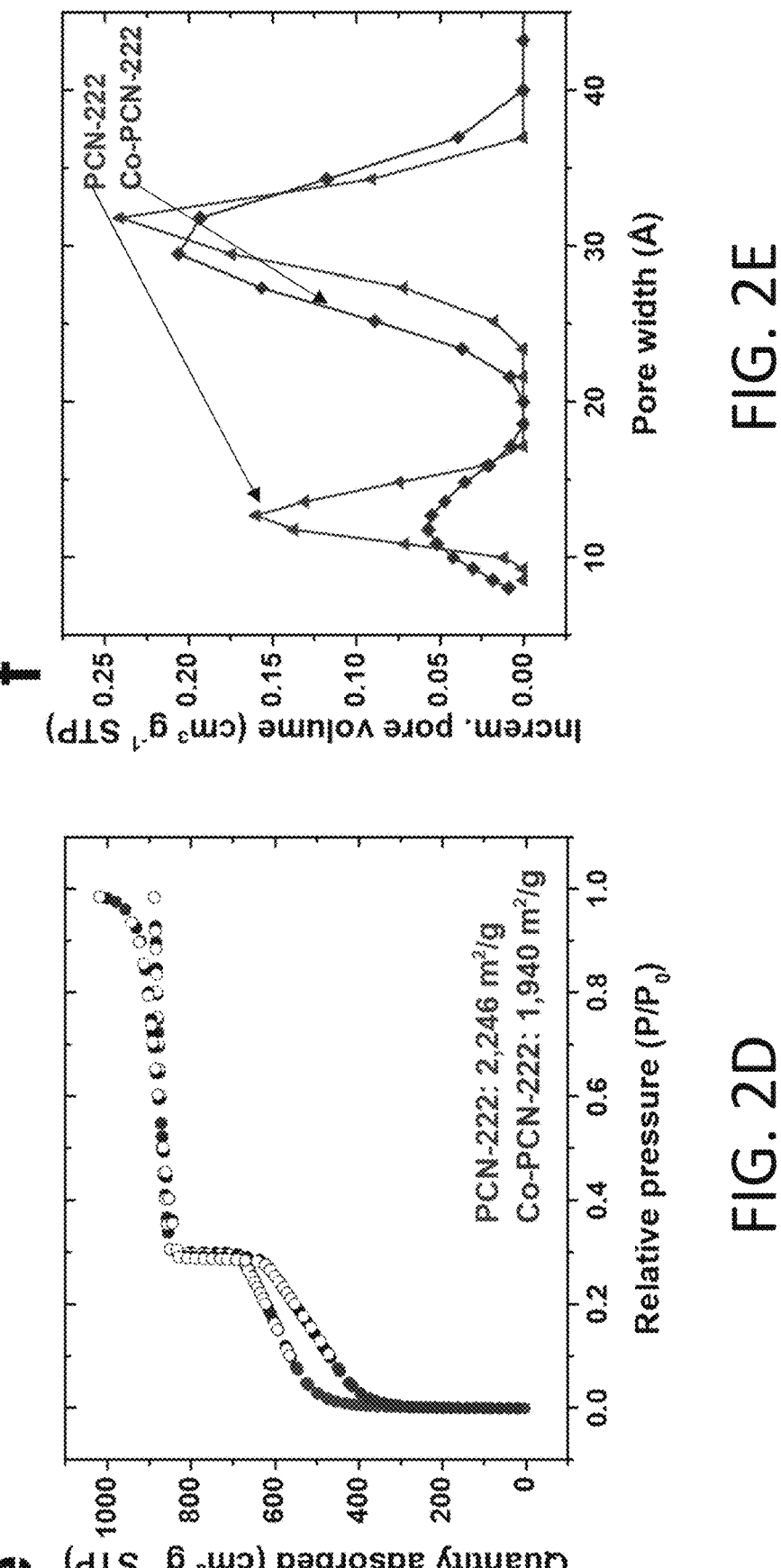
FIG. 2D shows $N_2$-sorption isotherms of PCN-222 and Co-PCN-222.
FIG. 2E shows pore size distributions of PCN-222 and Co-PCN-222.

We synthesized both Co-TCPP and Co-PCN-222 using previously published procedures. (Feng. D. W. et al., Angew. Chem. Int. Ed. 2012, 51 (41), 10307-10310; Jiao, L. et al., Nat. Commun. 2020, 11 (1), 2831.) The diffuse-reflectance (DR) UV-Vis absorption spectra of PCN-222 and Co-PCN-222 indicate that cobalt is retained in the final Co-PCN-222 material (as opposed to leaching during synthesis). The evidence for this conclusion is the coalescence of the four Q-bands in the PCN-222 spectrum into two Q-bands in the Co-PCN-222 spectrum due to the increase in symmetry from $D_{2h}$ to $D_{4h}$ upon metalation of the porphyrin (Carrasco, S. et al., Organometallics 2019, 38 (18), 3429-3435; Liu. E. et al., ACS Applied Nano Materials 2020, 3 (4), 3578-3584.) (FIG. 2A). We quantified the amount of incorporated cobalt using ICP-OES and found that there are 2.0 Co atoms/$Zr_6$ node, which is equivalent to 1.0 Co atoms/porphyrin linker. Therefore, based on the molecular formula of PCN-222 (two porphyrin linkers/node), we conclude that 100% of the porphyrin linkers in Co-PCN-222 are metalated. Furthermore, based on X-ray Photoelectron Spectroscopy (XPS), we conclude that the cobalt in Co-PCN-222 is predominantly Co(III) (FIG. 2B). The XPS spectrum of Co-PCN-222 lacks the characteristic satellite peaks of Co(II) species (as seen in the spectrum of the $CoCl_2 \cdot 6H_2O$ standard, red trace in FIG. 2B) and instead closely resembles the spectrum of $Co_3O_4$ nanoparticles, which are mostly Co(III). We estimate that ~80% of the cobalt is Co(III) based on fitting of the XPS spectrum of Co-PCN-222. Co-PCN-222 is highly crystalline according to PXRD analysis (FIG. 2C) and the crystallites possess the long, rod-like morphology typical of PCN-222. Finally. Co-PCN-222 displays $N_2$ sorption capacity. Brunauer-Emmett-Teller surface area, and pore size distribution similar to PCN-222, indicating that Co-PCN-222 is highly porous and possesses high internal surface area (FIGS. 2D and 2E). Relative to PCN-222, Co-PCN-222 exhibits a smaller microporous step in its isotherm and lower micropore volume in its pore size distribution, possibly due to orientation of axial ligands of Co(III) into the triangular pores. (Feng. D. W. et al., 2012.)

Co-PCN-222 is Highly Competent for the Selective Reduction of Acetylene to Ethylene.

Figures 3A, 3B:
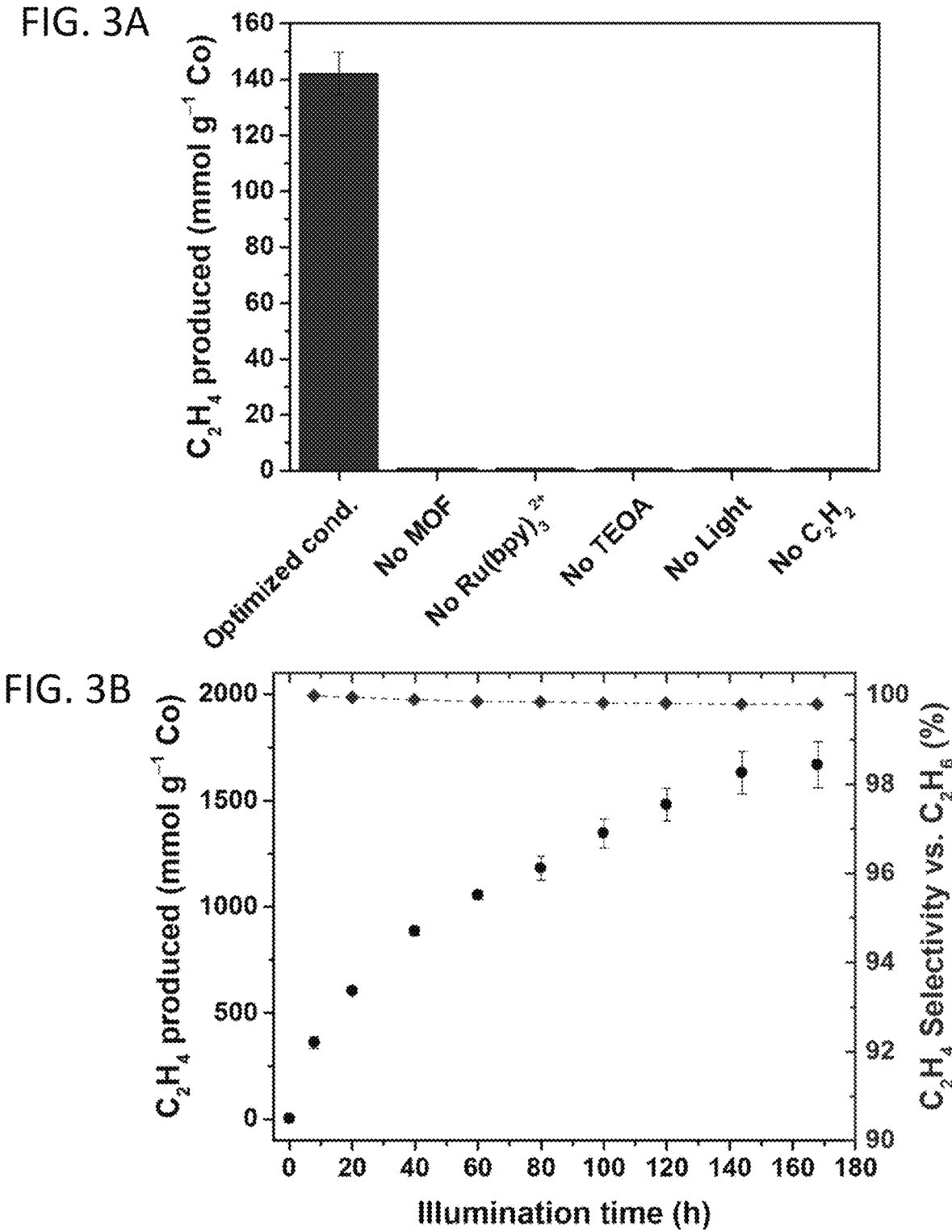
FIG. 3A shows total ethylene production for the "optimized" reaction mixture containing 2.5 mM (5 μmols) $Ru(bpy)_3^{2+}$, 0.8 mg (0.15 mM, 0.3 μmol) Co-PCN-222, and 1.25 M TEOA in acetonitrile under $C_2H_2$ (≥99.5 vol. %) irradiated (450 nm, 140 mW·cm$^{-2}$) for 4 h, and for reaction mixtures that differ from the optimized conditions as indicated by the axis labels.
FIG. 3B shows total ethylene production and selectivity as a function of irradiation time (450) nm) for the $Ru(bpy)_3^{2+}$/Co-PCN-222 system containing 10 mM $Ru(bpy)_3^{2+}$, 0.8 mg Co-PCN-222, 1.25 M TEOA in acetonitrile under $C_2H_2$ ($\geq$99.5 vol. %). Error bars represent the standard deviations for at least three separate experiments.
Figures 9, 10:
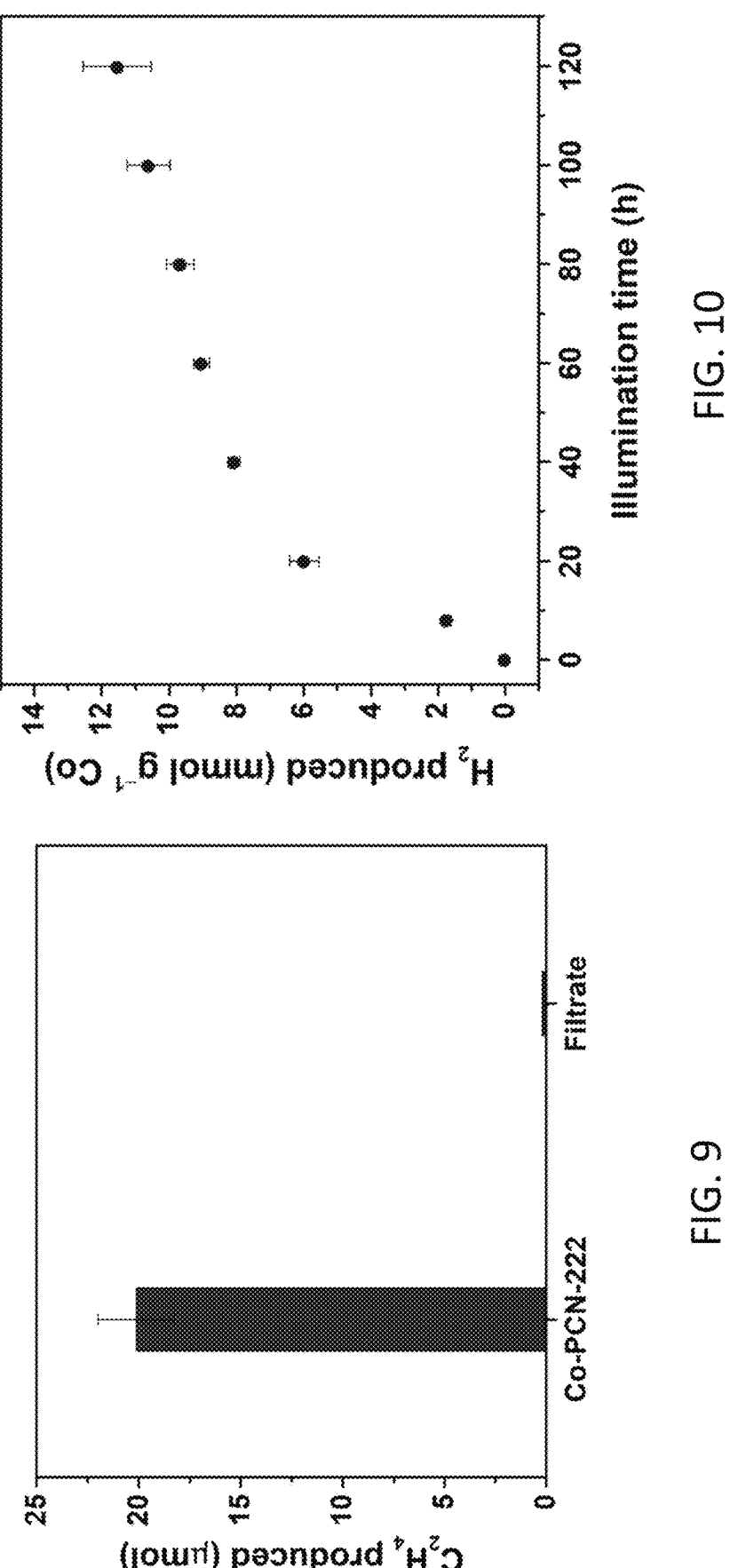
FIG. 9 shows ethylene production of the full reaction mixture and the supernatant of that reaction mixture. $C_2H_4$ produced (mmol g$^{-1}$ Co) by the $Ru(bpy)_3^{2+}$/Co-PCN-222 system and the filtrate after the reaction. The samples contain 2.5 mM $Ru(bpy)_3^{2+}$. 1.3 mg Co-PCN-222 and 1.25 M TEOA in acetonitrile under $C_2H_2$ ($\geq$99.5 vol. %) and were irradiated for 4 h. Error bars represent the standard deviations for at least three separate experiments.
FIG. 10 shows hydrogen production as a function of irradiation time. Production of $H_2$ (mmol g$^{-1}$ Co) for the $Ru(bpy)_3^{2+}$/Co-PCN-222 optimized reaction mixture containing 2.5 mM $[Ru(bpy)_3]^{2+}$, 0.8 mg Co-PCN-222, 1.25 M TEOA in acetonitrile under $C_2H_2$ ($\geq$99.5 vol. %). Error bars represent the standard deviations for at least three separate experiments.

Non-competitive conditions (pure acetylene, no ethylene co-feed): Our catalytic reaction mixture contains 0.8 mg (0.15 mM) Co-PCN-222 catalyst, 2.5 mM $Ru(bpy)_3^{2+}$ PS, and 1.25 M TEOA sacrificial donor in acetonitrile. In a typical experiment, we illuminated 2.0 mL of this mixture under 1 atm $C_2H_2$ (≥99.5 vol. %) using a 450-nm light-emitting diode (LED. 140 mW·cm$^{-2}$); the details of the purging and photocatalytic setups are published elsewhere. (Arcudi. F. et al., 2022.) The semihydrogenation of acetylene does not proceed in the absence of any of these components, which confirms the photocatalytic nature of the reaction (FIG. 3A and Table 1). A typical gas chromatogram and mass spectrum of the reaction mixture after 4 hours of irradiation shows conversion of acetylene to ethylene without appreciable over-hydrogenation to ethane (FIGS. 8A-8D). To confirm that the observed catalysis was due to Co-PCN-222 (as opposed to homogeneous Co that leached into solution), we conducted "hot filtration experiments", in which we illuminated the full reaction mixture for 4 hours, removed the MOF via centrifugation and syringe filtration, and continued illuminating the supernatant for an additional 70 hours. We observe almost no additional conversion of $C_2H_2$ to $C_2H_4$ from the supernatant, which confirms that catalysis is due to Co in Co-PCN-222 and that Co-TCPP remains in the crystallites (FIG. 9). ICP-OES analysis also indicates that Co leaching from Co-PCN-222 is negligible during photocatalysis (Table 2). In fact, we observe an increase in the Co/Zr ratio in the MOF following catalysis, which implies that Zr, not Co, is selectively leached from the material.

While high concentrations of TEOA appear to negatively impact the structural integrity of Co-PCN-222, cessation of catalysis is primarily due to the degradation of $Ru(bpy)_3^{2+}$. Following catalysis, PXRD patterns of Co-PCN-222 show a loss of crystallinity, and $N_2$ sorption isotherms reveal an almost complete loss of porosity. SEM images, however, display almost no change in particle morphology, even after

TABLE 1

Photocatalytic and control reactions for $C_2H_2$ to $C_2H_4$ reduction by the $Ru(bpy)_3^{2+}$/Co-PCN-222 system.

| Entry | Reaction Conditions | $C_2H_4$ (mmol $g^{-1}$) | Sel. $C_2H_4$ vs. $C_2H_6$ (%) | $H_2$ (mmol $g^{-1}$) |
|---|---|---|---|---|
| 1 | Co-PCN-222 + $Ru(bpy)_3^{2+}$ + TEOA | 142.1 | 99.5 | 0.52 |
| 2 | $Ru(bpy)_3^{2+}$ + TEOA (no MOF) | trace | — | n.d. |
| 3 | Co-PCN-222 + TEOA (no $Ru(bpy)_3^{2+}$) | trace | — | n.d. |
| 4 | Co-PCN-222 + $Ru(bpy)_3^{2+}$ (no TEOA) | trace | — | n.d. |
| 5 | Co-PCN-222 + $Ru(bpy)_3^{2+}$ + TEOA (no light) | trace | — | n.d. |
| 6 | Co-PCN-222 + $Ru(bpy)_3^{2+}$ + TEOA (no $C_2H_2$) | trace | — | n.d. |
| 7 | Co-PCN-222 + $Ru(bpy)_3^{2+}$ + TEOA + TEMPO | trace | — | n.d. |

Summary of the reaction conditions used for the photocatalytic and control experiments. In a typical reaction, 2.0 mL of a $C_2H_2$ (≥99.5 vol. %)-purged solution (entries 1-5, 7) or He-purged solution (entry 6) containing photocatalyst (0.8 mg Co-PCN-222, entries 1, 3-7), photosensitizer (2.5 mM $Ru(bpy)_3^{2+}$, entries 1-2, 4-7), sacrificial donor (1.25 M TEOA, entries 1-3, 5-7), TEMPO (200 equiv. vs. Co-PCN-222, entry 6) were irradiated at 450 nm (140 $mW \cdot cm^{-2}$) for 4 h (entries 1-4, 6-7) or stirred in the dark for 4 h (entry 5). Products were detected via GC-TCD or GC-MS analysis and experiments were performed at least in duplicate.

72 hours of reaction. PXRD patterns of Co-PCN-222 and absorbance spectra of the supernatant after selective exposure of Co-PCN-222 to various components of the reaction mixture indicate that TEOA is responsible for framework degradation. We stress, however, that the loss of crystallinity over the course of the reaction is not the reason catalysis stops. Re-addition experiments show that catalysis recovers more upon the addition of $Ru(bpy)_3^{2+}$; or TEOA than Co-PCN-222. These results imply that the photodegradation of $Ru(bpy)_3^{2+}$ and depletion of TEOA are more important factors in the loss of conversion than degradation of the

TABLE 2

ICP-OES results for pre- and post-catalysis samples.

| Sample | Measured [Zr] (mg $L^{-1}$) | Measured [Co] (mg $L^{-1}$) | Moles Zr | Moles Co | Co/$Zr_6$ Node |
|---|---|---|---|---|---|
| Pre-catalysis (0 h) | 7.80 | 1.69 | $8.59 \cdot 10^{-7}$ | $2.88 \cdot 10^{-7}$ | 2.01 |
| Post-catalysis (4 h) | 3.23 | 0.85 | $3.62 \cdot 10^{-7}$ | $1.48 \cdot 10^{-7}$ | 2.45 |
| Post-catalysis (72 h) | 3.16 | 0.82 | $3.54 \cdot 10^{-7}$ | $1.42 \cdot 10^{-7}$ | 2.41 |

Figure 11A:
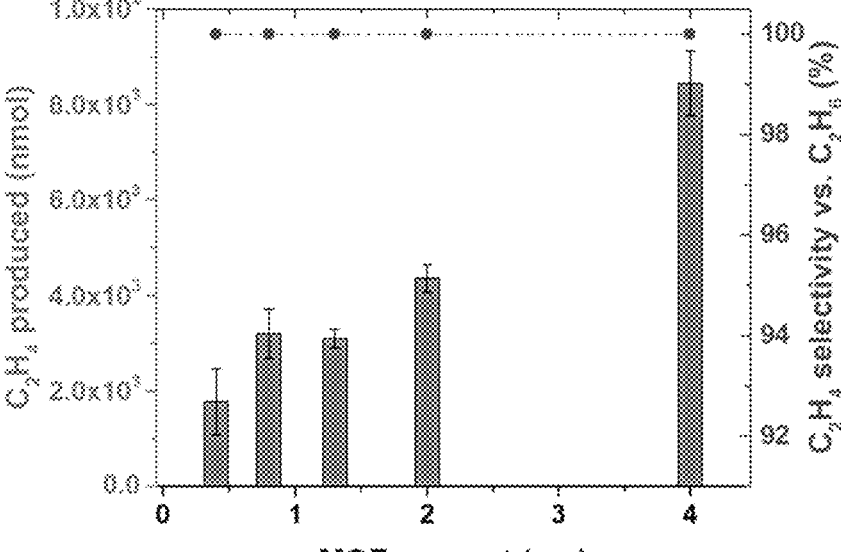
FIGS. 11A-11C show photocatalytic performance through variation of amount of Co-PCN-222. Optimization of $C_2H_4$ selectivity vs. $C_2H_6$ and $C_2H_4$ produced on a (FIG. 11A) nmol scale and (FIG. 11B) mmol g$^{-1}$ Co scale through variation of amount of Co-PCN-222 (mg).
Figure 11B:
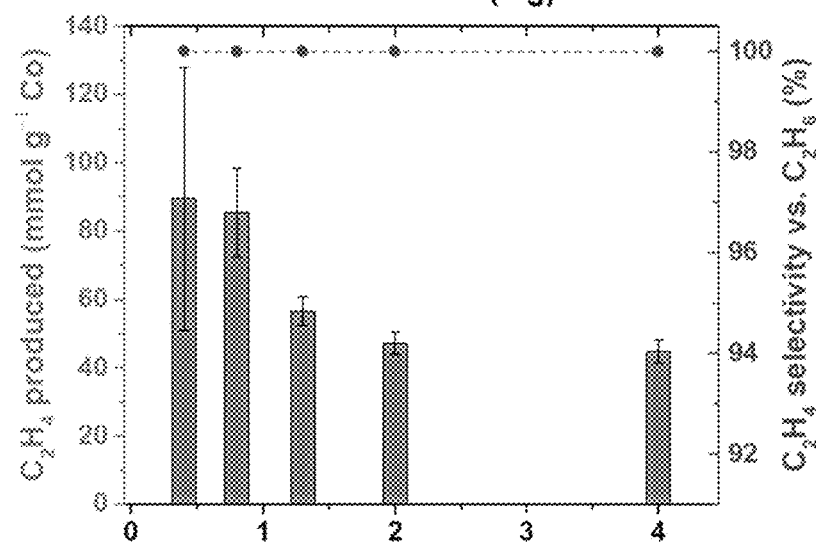
Figure 11C:
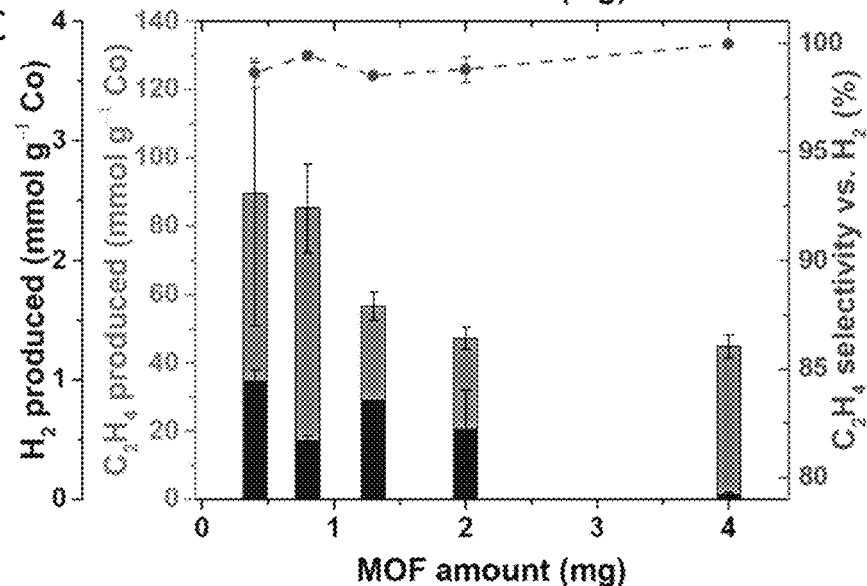
Figure 12:
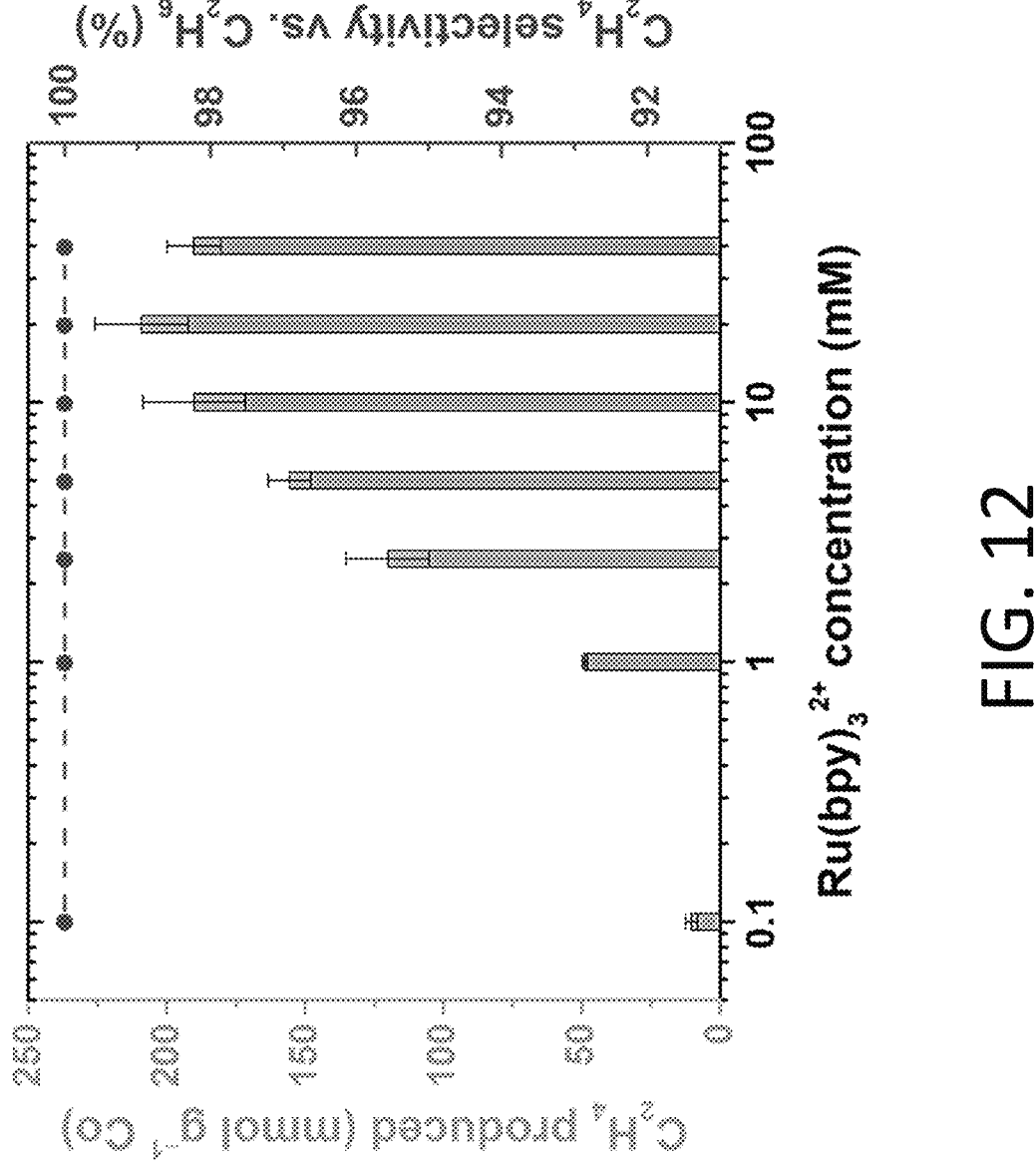
FIG. 12 shows photocatalytic performance through variation of concentration of $Ru(bpy)_3^{2+}$. Optimization of $C_2H_4$ selectivity vs. $C_2H_6$ and $C_2H_4$ produced (mmol g$^{-1}$ Co) by the $Ru(bpy)_3^{2+}$/Co-PCN-222 MOF system in acetonitrile under $C_2H_2$ ($\geq$99.5 vol. %) irradiated for 4 h through variation of concentration (mM) of $Ru(bpy)_3^{2+}$ in the presence of 0.8 mg Co-PCN-222 and 1.25 M TEOA. Error bars represent the standard deviations for at least three separate experiments.
Figure 13:
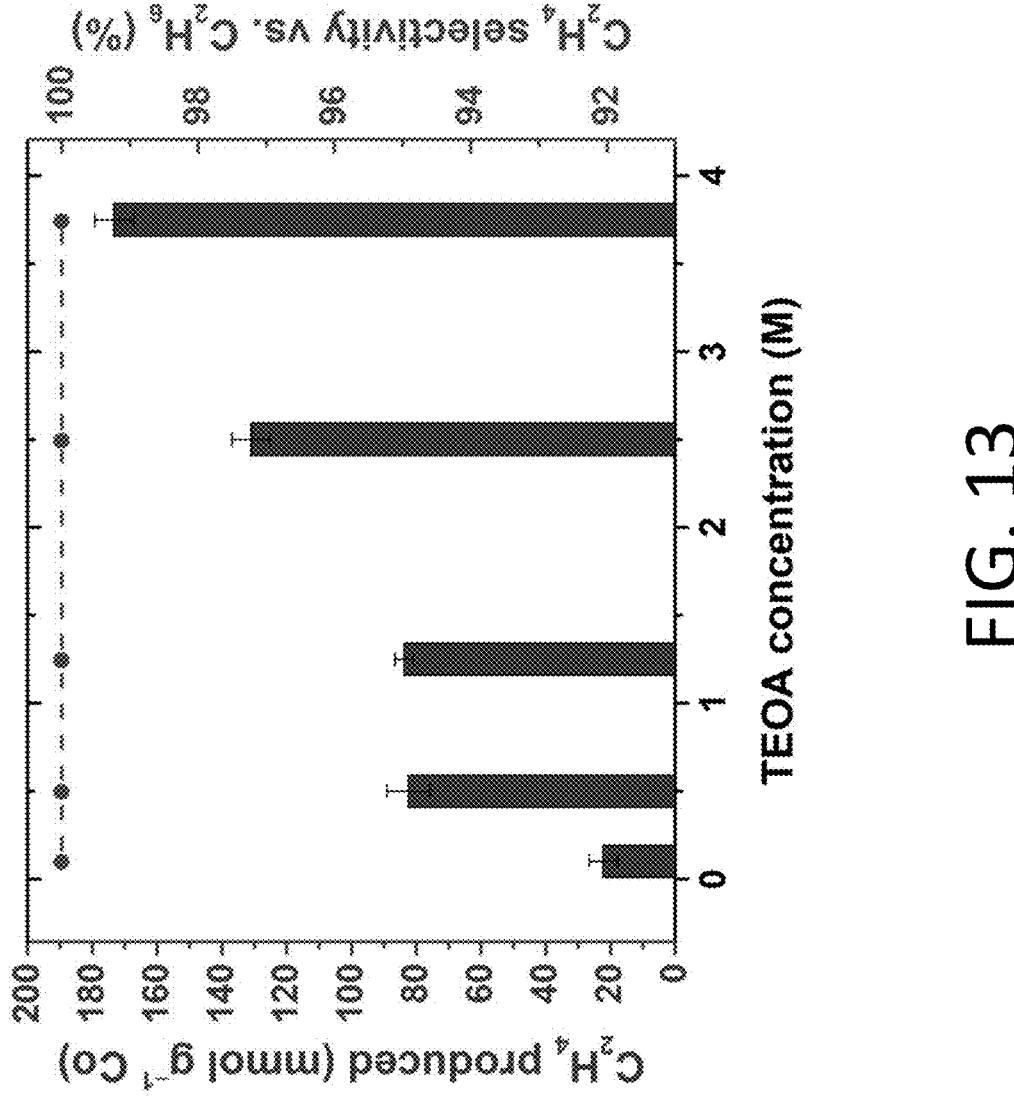
FIG. 13 shows photocatalytic performance through variation of concentration of TEOA. Optimization of $C_2H_4$ selectivity vs. $C_2H_6$ and $C_2H_4$ produced (mmol g$^{-1}$ Co) by the $Ru(bpy)_3^{2+}$/Co-PCN-222 MOF system in acetonitrile under $C_2H_2$ ($\geq$99.5 vol. %) irradiated for 4 h through variation of concentration (M) of TEOA in the presence of 1.25 mM $Ru(bpy)_3^{2+}$ and 0.8 mg Co-PCN-222. Error bars represent the standard deviations for at least three separate experiments.

We anticipated that a main strength of our heterogeneous Co-PCN-222 catalyst would be longevity compared to a homogeneous system, in which ethylene production saturates after 24 hours due to the degradation of the photocatalytic mixture. Indeed, our catalytic mixture remains productive over the course of one week of illumination, achieving selectivity for ethylene over ethane of >99.7% and overall production of more than 1.6 moles $C_2H_4$ per gram of Co after 168 hours (FIG. 3B). We observe concurrent $H_2$ evolution from our system, but in small quantities (11.5 mol $g^{-1}$ Co after 120 hours, at which point $H_2$ production saturates), such that the overall selectivity for ethylene remains >99.0% (FIG. 10). Increasing the amount of Co-PCN-222 increases the number of moles of $C_2H_4$ produced, but decreases the number of moles of $C_2H_4$ produced per gram Co (FIGS. 11A-11C). Increasing the concentration of $Ru(bpy)_3^{2+}$ improves production of $C_2H_4$, but this improvement plateaus above 10 mM $Ru(bpy)_3^{2+}$ (FIG. 12). The amount of $C_2H_4$ produced increases with increasing TEOA concentration up to 1.25 M, but decreases at higher TEOA concentrations (FIG. 13), most likely due to a loss of crystallinity in the Co-PCN-222 framework (vide infra).

Figure 14:
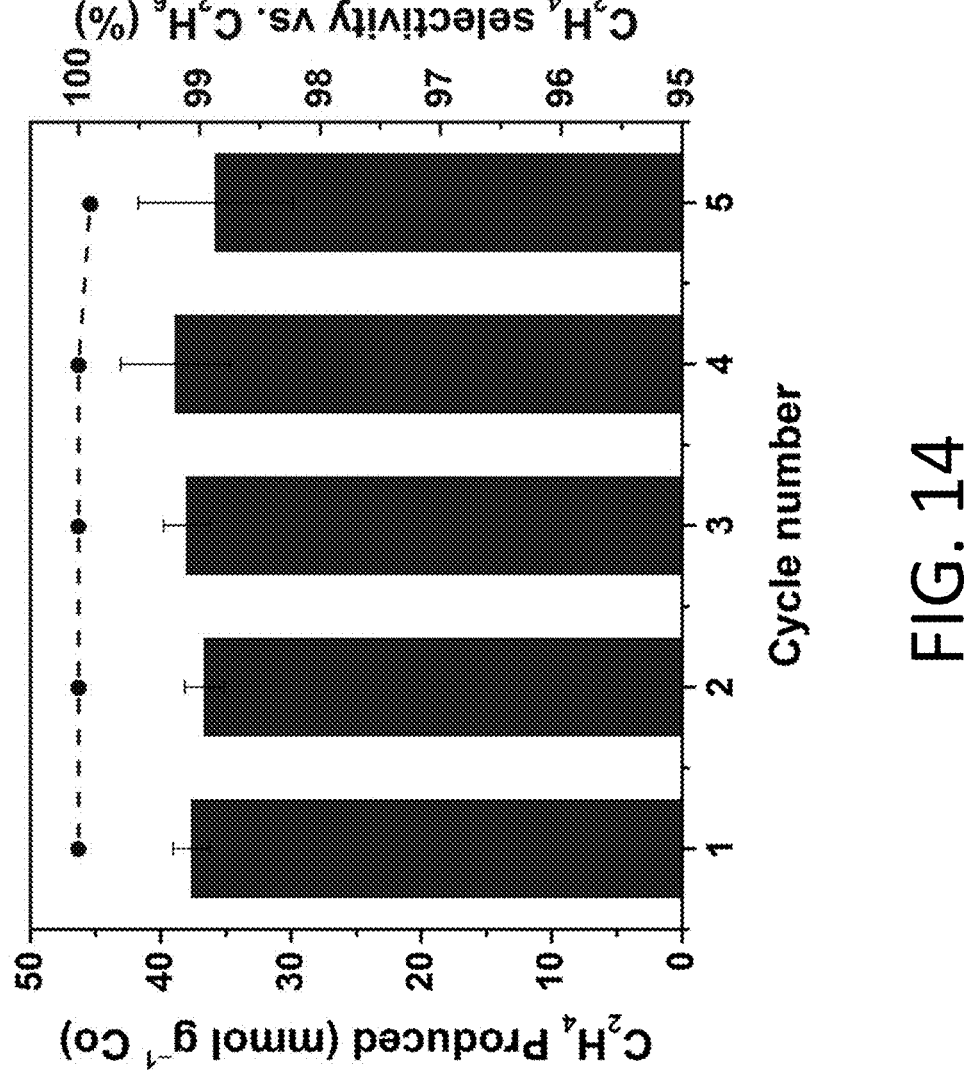
FIG. 14 shows recyclability of the Co-PCN-222 photocatalyst for ethylene production. $C_2H_4$ produced (mmol g$^{-1}$ Co) and $C_2H_4$ selectivity vs. $C_2H_6$ by the $Ru(bpy)_3^{2+}$/Co-PCN-222 system in acetonitrile under $C_2H_2$ ($\geq$99.5 vol. %) irradiated for 4 h each cycle containing 2.5 mM $Ru(bpy)_3^{2+}$, 0.8 mg Co-PCN-222 and 1.25 M TEOA. For cycles 2-5, the used catalyst is recovered and redispersed in a fresh solution containing 2.5 mM $Ru(bpy)_3^{2+}$ and 1.25 M TEOA in acetonitrile. Error bars represent the standard deviations for at least three separate experiments.

Co-PCN-222 framework. This conclusion is corroborated by the drastic changes observed in the absorption spectrum of $Ru(bpy)_3^{2+}$ after just four hours of illumination, indicating significant photodegradation of $Ru(bpy)_3^{2+}$. Furthermore, the loss of long-range order does not inhibit the isolation of Co-PCN-222 from the reaction mixture, and we demonstrate it is possible to recycle Co-PCN-222 for a minimum of five cycles (FIG. 14).

We note that the deviation from linearity in the ethylene production kinetic is concurrent with the loss in crystallinity observed in PXRD, after ~20 hours. We conclude that while the amorphous material that is present at later reaction times is still catalytically active, the long-range order and porosity of Co-PCN-222 help facilitate catalysis at early times. We hypothesize that, as the reaction progresses and the porosity collapses, fewer internal Co sites are accessible, leading to a decrease in activity.

Figure 4A:
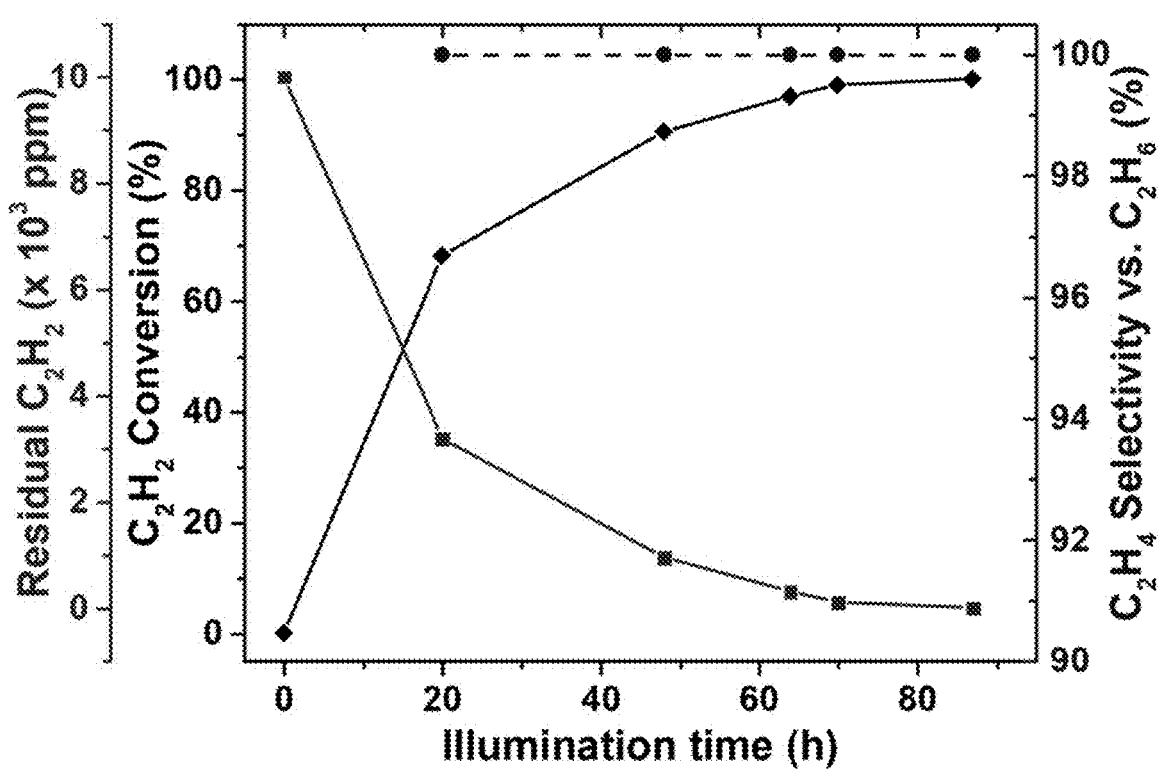
FIGS. 4A-4B show performance of the $Ru(bpy)_3^{2+}$/Co-PCN-222 system containing 8 mg (1.5 mM) Co-PCN-222, 10 mM $Ru(bpy)_3^{2+}$, and 1.25 M TEOA under a $C_2H_2$/$C_2H_4$ mixture (1 vol. % $C_2H_2$, 30 vol. % $C_2H_4$, He balance).
Figure 4B:
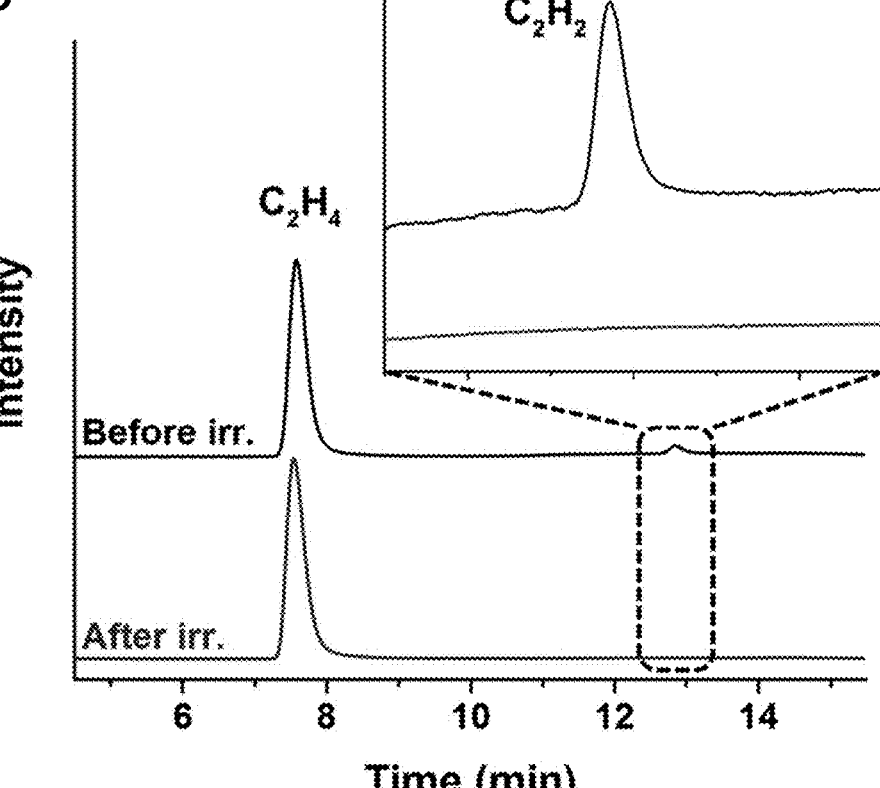
Figure 15:
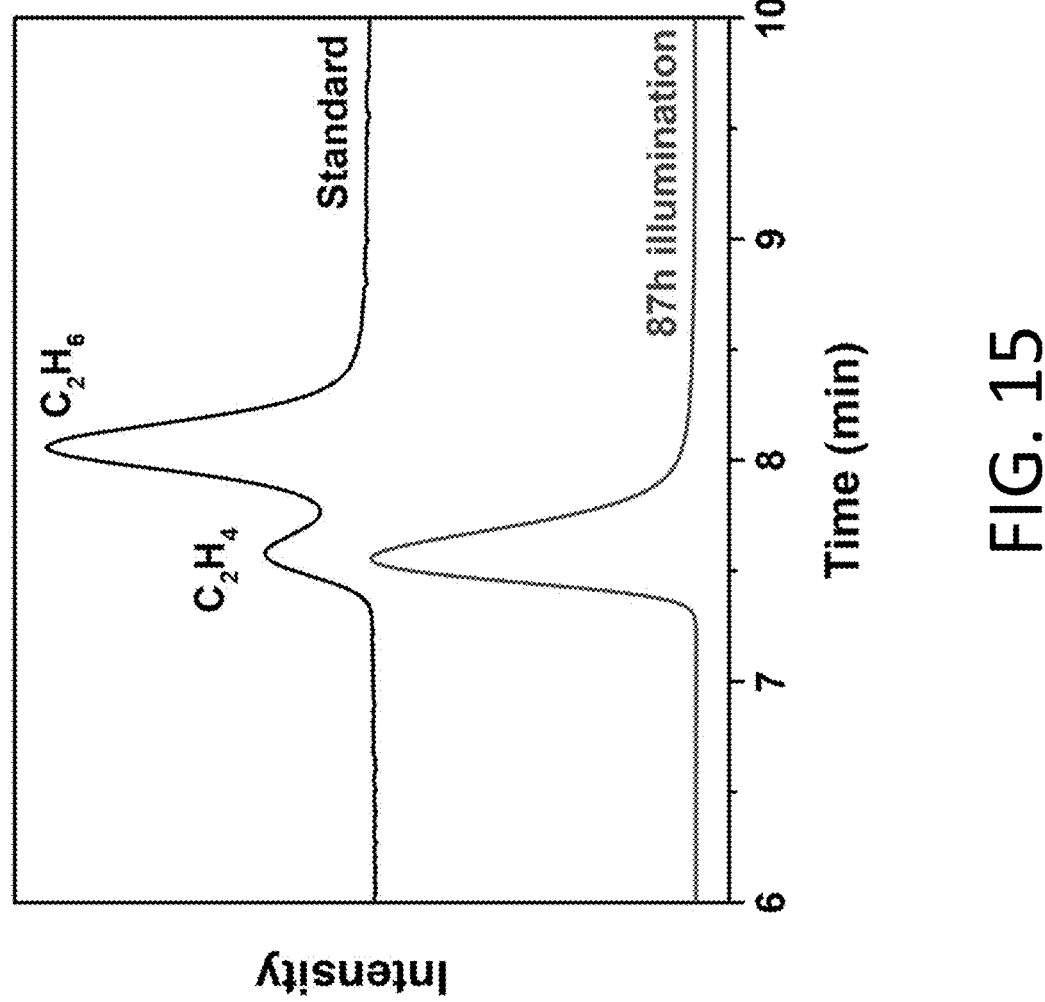
FIG. 15 shows typical GC-FID chromatograms for the photoreduction of the ethylene/acetylene mixture. GC chromatograms of $C_2H_4$ and $C_2H_6$ standard (black) and the headspace composition of the $Ru(bpy)_3^{2+}$/Co-PCN-222 system in acetonitrile under $C_2H_2$/$C_2H_4$ (1 vol. % $C_2H_2$, 30 vol. % $C_2H_4$, He balance) mixture irradiated for 87 h containing 10 mM $Ru(bpy)_3^{2+}$, 8.0 mg Co-PCN-222 and 1.25 M TEOA (grey).
Figures 16A, 16B, 16C, 16D:
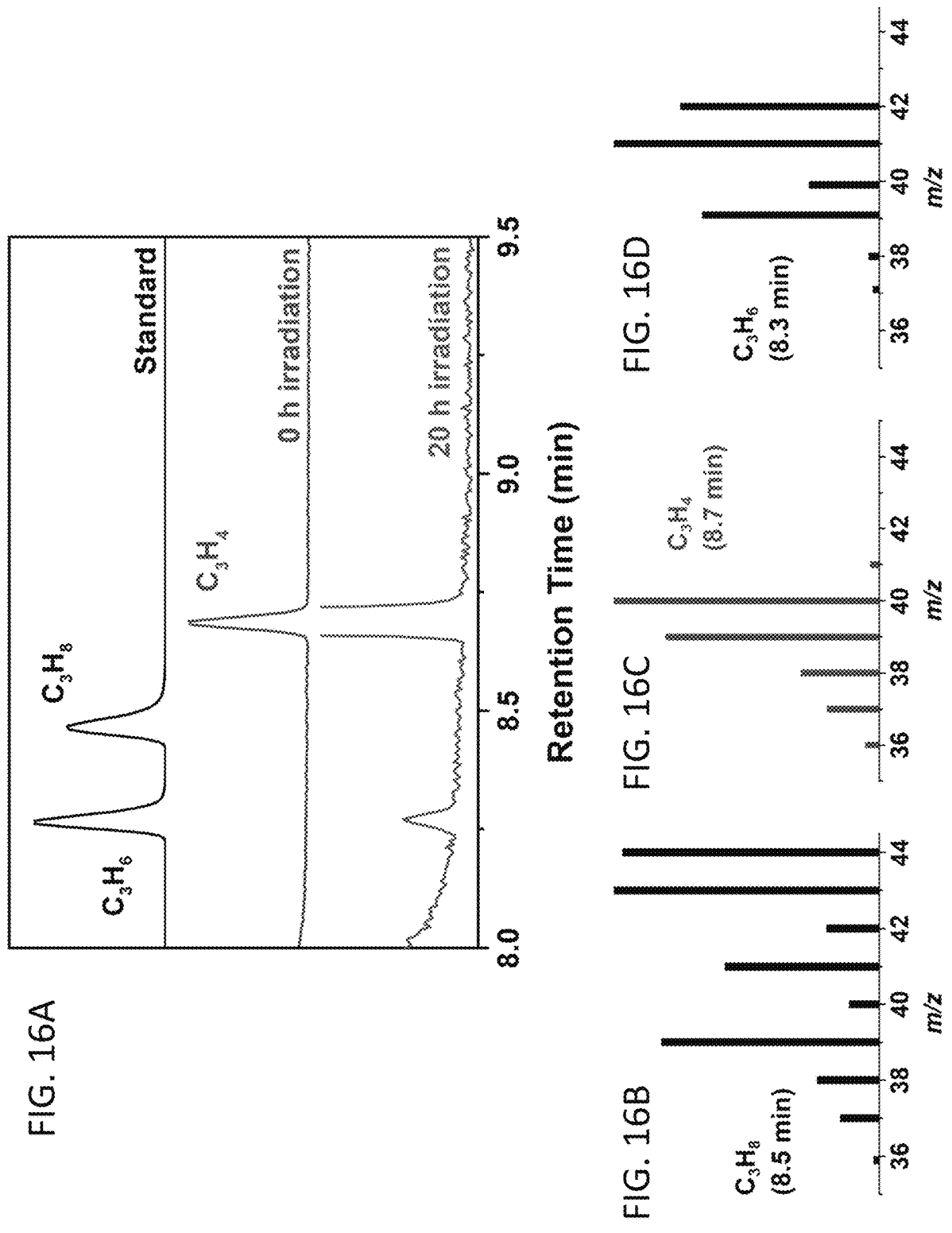
FIGS. 16A-16D show typical GC-MS chromatograms for the photoreduction of propyne.

Competitive conditions (ethylene co-feed): Importantly, our $Ru(bpy)_3^{2+}$-sensitized Co-PCN-222 system selectively reduces acetylene into ethylene even in the presence of excess ethylene (1 vol. % $C_2H_2$, 30 vol. % $C_2H_4$. He balance). This ethylene/acetylene mixture represents a typical industrial ethylene feed and a highly selective catalyst is required to avoid over-hydrogenation to ethane. Our system achieves near 100% conversion of acetylene to ethylene with >99.9% selectivity for ethylene over ethane after 87 hours of illumination (FIG. 4). Crucially, we observe no over-hydrogenation to ethane over the illumination time (FIG. 15). Our system also converts propyne into propylene without producing propane (FIGS. 16A-16D). Similar to ethylene, the production of pure propylene streams cannot be accomplished by industrial steam cracking. This result shows that our photocatalytic system produces both polymer-grade ethylene and propylene, which together account for ~80% of global plastics demand. (Geyer. R. et al., 2017.)

Proposed Mechanism. Our proposed mechanism for the photocatalytic semihydrogenation of acetylene to ethylene using Co-PCN-222 is shown in FIG. 5A. There are three pieces of evidence that inform this mechanism: (i) decreased $H_2$ evolution from Co-PCN-222 under competitive vs. non-competitive conditions; (ii) complete cessation of the reaction in the presence of the radical trap TEMPO; and (iii) comparable rates of $Ru(bpy)_3^{2+}$ luminescence quenching by Co-PCN-222 and TEOA.

As discussed above, our photocatalytic system evolves a small amount of $H_2$ during the semihydrogenation of acetylene to ethylene. The amount of $H_2$ evolved, however, is drastically reduced when the reaction is run under 99.5% $C_2H_2$ atmosphere as opposed to under Ar atmosphere (FIG. 5B). This result suggests that $H_2$ evolution and $C_2H_2$ reduction proceed via the same intermediate—under conditions where there is competition for the intermediate, the $H_2$ evolution reaction is outcompeted by $C_2H_2$ reduction. Photocatalytic $H_2$ evolution with Co-based catalysts (and even Co-based MOFs) proceeds through a cobalt-hydride ($Co^{III}$—H) intermediate. (Pattengale, B. et al., *ACS Catal.* 2017, 7 (12), 8446-8453; Michiyuki, T. et al., *Asian Journal of Organic Chemistry* 2020, 9 (3). 343-358; Delley, M. F. et al., *J. Am. Chem. Soc.* 2019, 141 (38). 15390-15402. Consequently, we conclude that the $C_2H_2$ reduction in our Co-PCN-222 system proceeds through a $Co^{III}$—H intermediate as well.

Figures 5C, 5D:
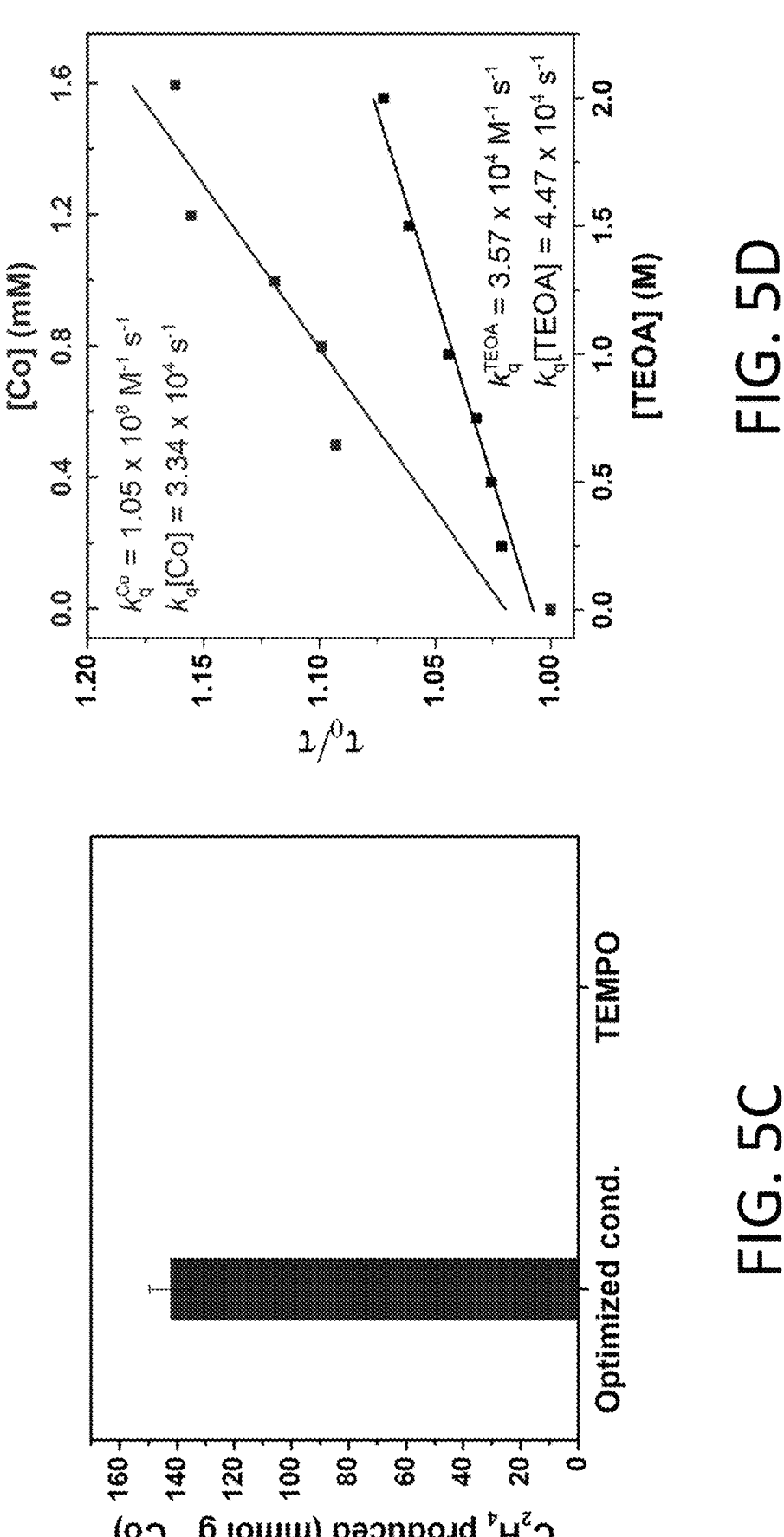
FIG. 5C shows comparison of ethylene production by the Ru/Co-PCN-222 system under optimized conditions and in the presence of 200 molar equiv. TEMPO with respect to Co-PCN-222.
FIG. 5D shows a Stern-Volmer plot of $Ru(bpy)_3^{2+}$ luminescence quenching in the presence of Co-PCN-222 (grey) and TEOA (black).

We observe no $C_2H_2$ reduction when we run the reaction in the presence of the radical trap TEMPO, which suggests the presence of a radical intermediate (FIG. 5C). There are two generally accepted mechanisms by which the insertion of unsaturated hydrocarbons into M-H bonds can occur: migratory insertion and hydrogen atom transfer (HAT). (de Bruin, B. et al., *Chem Eur.* 2009, 15 (17), 4312-4320.) The HAT pathway generates a radical intermediate, so we conclude that $C_2H_2$ inserts into the $Co^{III}$—H bond via HAT.

Finally, we observe that Co-PCN-222 and TEOA quench the photoluminescence of $Ru(bpy)_3^{2+}$ with comparable rates (FIG. 5D). While previous studies have shown that the unimolecular rate constant for $Ru(bpy)_3^{2+}$ luminescence quenching is a factor of 1000 times greater for TEOA than for the photocatalyst, we observe unimolecular rate constants that differ by only a factor of 1.5 in favor of TEOA. (Arcudi, F. et al., 2022.) The similarity of the rates implies that both TEOA and the photocatalyst contribute to the quenching of $Ru(bpy)_3^{2+}$ luminescence in our system.

Previous works on photocatalysis with $Co^{III}$-porphyrins employ sodium ascorbate (NaAsc) as the sacrificial donor. In the proposed mechanisms in these studies, NaAsc acts not only as donor, but as a chemical reductant to initially reduce $[Co^{III}P]$ to $[Co^{II}P]$, which is subsequently reduced to $[Co^{I}P]$ by photogenerated $[Ru(bpy)_2(bpy)^{\cdot-}]^+$ (reduction potential=−1.45V vs. SCE). (Arcudi, F. et al., 2022; Call, A. et al., *ACS Catal.* 2019, 9 (6), 4867-4874; Call. A. et al., Sustainable Energy & Fuels 2022, 6 (9), 2160-2164.) In our system, however, TEOA does not chemically reduce $Co^{III}$-TCPP to $Co^{II}$-TCPP, as evidenced by the unchanged position of the Soret band in the UV-Vis absorption spectrum of Co-TCPP linker in the presence or absence of TEOA. From this result and the observed luminescence quenching in the presence of Co-PCN-222, we propose that a pair of photogenerated $[Ru(bpy)_2(bpy)^{\cdot-}]^+$ species reduce Co-PCN-222 twice, reducing the linker from $Co^{III}$-TCPP to $Co^{II}$-TCPP and subsequently from $Co^{II}$-TCPP to $Co^{I}$-TCPP. A previous study of the Co-TCPP linker in the MOF Co-PIZA measured the $Co^{III}$-TCPP/$Co^{II}$-TCPP and $Co^{II}$-TCPP/$Co^{I}$-TCPP reduction potentials as $E_{1/2}$=−0.54 V vs. SCE and $E_{1/2}$=−0.92 V vs. SCE, respectively, both of which are well within the reduction potential of $[Ru(bpy)_2(bpy)^{\cdot-}]^+$. (Ahrenholtz, S. R. et al., *J. Am. Chem. Soc.* 2014, 136 (6), 2464-2472.) We additionally propose that $Ru(bpy)_3^{2+}$ undergoes reductive quenching to form $[Ru(bpy)_2(bpy)^{\cdot-}]^+$, as is common with aliphatic amines in high concentrations. (Pellegrin, Y. et al., *Comptes Rendus Chimie* 2017, 20 (3), 283-295; Prier, C. K. et al., *Chem. Rev.* 2013, 113 (7), 5322-63; Sun, H. et al., *J. Phys. Chem.* 1994, 98 (45), 11719-11726; Narayanam, J. M. R. et al., *Chem. Soc. Rev.* 2011, 40 (1), 102-113.)

We note that one step in the TEOA degradation pathway following electron transfer to PS involves the formation of a carbon-centered radical that is a powerful reductant (−1V vs. SCE). (DeLaive, P. J. et al., *J. Am. Chem. Soc.* 1980, 102 (17), 5627-5631.) We therefore cannot exclude that this carbon-centered radical could also contribute to the reduction of $Co^{III}$-TCPP to $Co^{I}$-TCPP, as has been reported previously. (Probst, B. et al., *Inorg. Chem.* 2010, 49 (14), 6453-6460.)

Overall, our proposed mechanism is as follows: following photoexcitation of $Ru(bpy)_3^{2+}$ and reductive quenching of $[Ru(bpy)_3^{2+}]^*$ by TEOA, the resulting $[Ru(bpy)_2(bpy)^{\cdot-}]^+$ reduces $Co^{III}$-TCPP in Co-PCN-222 twice to form $Co^{I}$-TCPP. $Co^{I}$-TCPP accepts a proton from the oxidized $TEOA^{\cdot+}$, to form a $Co^{III}$—H intermediate. $C_2H_2$ then inserts into the $Co^{III}$—H bond via hydrogen atom transfer. An additional proton and electron are supplied by TEOA/$TEOA^{\cdot+}$. Finally, $C_2H_4$ is released, and $Co^{III}$-TCPP is regenerated.

Materials and Methods

Safety Warning

Acetylene is an extremely flammable gas. Buildup of acetylene vapors can result in fire or explosions if triggered by sparks. Acetylene may displace oxygen and cause rapid suffocation. In our experimental setup, the acetylene cylinder was fitted with a CGA 510 regulator equipped with a flashback arrestor and connected, through stainless steel tubing and a flow regulator, to a purging station that was placed inside a fume hood. (Arcudi, F. et al., *Nat Chem* 2022, 14 (9), 1007-1012.) A Snoop® solution was applied to fittings and joints to inspect for leaks, until no bubble formation was observed. There was no electrical equipment in the fume hood.

Materials

Pyrrole (>99%, TCI), methyl 4-formylbenzoate (99%, Aldrich), Propionic acid (99%, Sigma-Aldrich), cobalt chloride hexahydrate (98%, Alfa Aesar), chloroform (Fisher), magnesium sulfate (anhydrous, Fisher), tetrahydrofuran (Fisher), methanol (Fisher), hydrogen chloride (37%, Sigma-Aldrich), zirconyl chloride octahydrate ($ZrOCl_2 \cdot 8H_2O$, reagent grade 98%, Sigma-Aldrich), trifluoroacetic acid (TFA, ReagentPlus® 99%, Sigma-Aldrich), N,N-dimethylformamide (DMF, 99.8%, Fisher), acetonitrile (ACN, anhydrous 99.8%, Sigma-Aldrich), triethanolamine (TEOA, >99.0%, Sigma-Aldrich), tris(2,2'-bipyridyl)dichlo-roruthenium(II) hexahydrate (Ru(bpy)$_3^{2+}$, 99.95%, Sigma-Aldrich), triethylamine (TEA, HPLC grade, Fisher), (2,2,6,6-tetramethylpiperidin-1-yl)oxyl (TEMPO, 99%, Sigma-Aldrich), propyne (≥99 vol. %, Sigma-Aldrich) and cobalt nanoparticles (cobalt(II,III) oxide, 99.5%, <50 nm, Sigma-Aldrich) were used as received. Ultrapure water (>18.25 MΩ cm) was obtained using a Thermo Scientific Barnstead GenPure Pro.

Synthesis of Co-PCN-222

[meso-tetra(4-carboxyphenyl)porphyrinato]-cobalt(II)] (Co-TCPP) and subsequently Co-PCN-222[3] were synthesized according to published procedures. (Feng, D. et al., *Angew. Chem. Int. Ed.* 2012, 51 (41), 10307-10310.)

Photocatalytic Reactions

Samples were prepared in a 7.5 mL screw cap vial (GLC-00985, Qorpak) equipped with a micro stir bar (7 mm, Fisher Scientific) and sealed with silicone/PTFE septum (TS-12713, Thermo Scientific) and cap (open top, TS-13216, Thermo Scientific). Vials were sealed and purged, through a flow regulator (at 130 mm), either for (i) 10 minutes with He (or Ar) followed by 5 minutes with C$_2$H$_2$ (≥99.5 vol. %, Airgas) or (ii) for 15 minutes with C$_2$H$_4$/C$_2$H$_2$ mixture (1 vol. % C$_2$H$_2$, 30 vol. % C$_2$H$_4$, He balance, Airgas) or (iii) 15 minutes with Ar or (iv) 15 minutes with He followed by injecting C$_3$H$_4$ (350 μL with gas-tight Hamilton syringe of ≥99 vol. % C$_3$H$_4$, Sigma-Aldrich) by using steel needles inserted through the septum as inlet (inserted into the solution) and outlet (venting the headspace to the surrounding atmosphere). After purging for the time specified above, the pressure of the headspace was then equilibrated to 1 atm. The vials were then illuminated using a homebuilt photoreactor made of royal blue (450 nm) LEDs (Cree XLamp XP-E2 Color High Power LED Star, LED-supply.com) with a light intensity of 140 mW·cm$^{-2}$ (measured using an Optical Power Meter PM100D with Optical Sensor S120VC from Thorlabs). Each vial was suspended on top of a single LED, equipped with a lens, using a homebuilt sample holder. The vials were continuously stirred at 600 rpm during the irradiation.

Chromatographic Detection of Gases

Figure 6A:
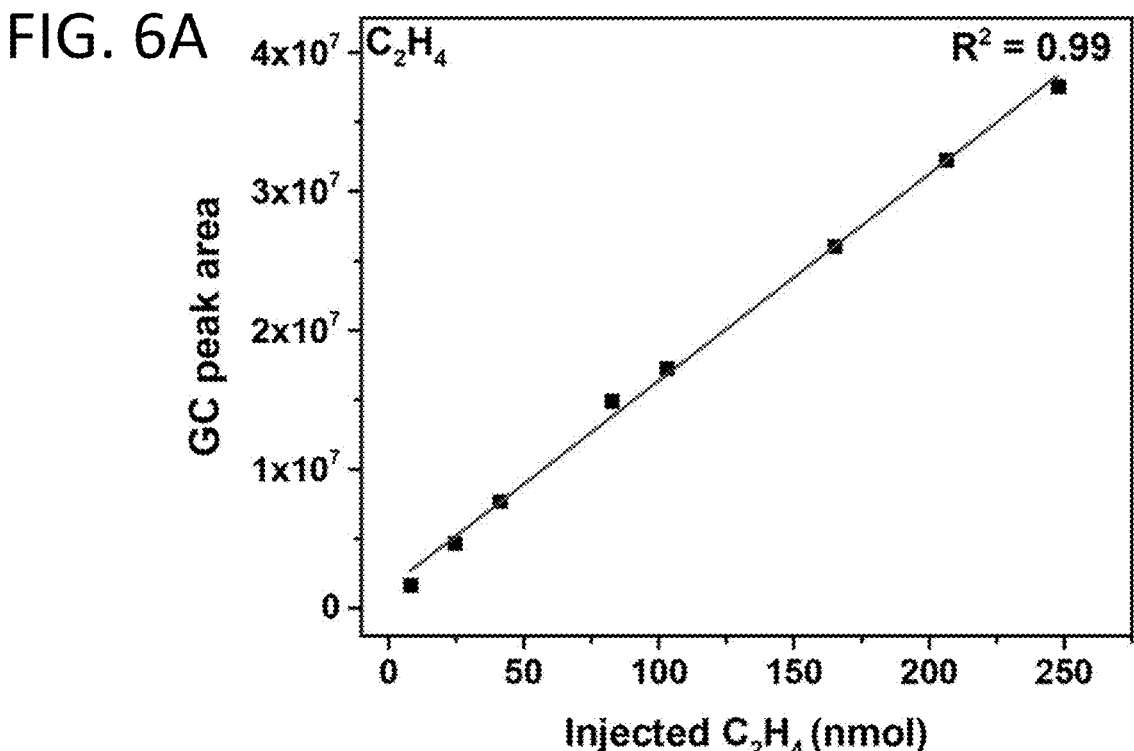
FIGS. 6A-6B show calibration curves for quantification of gaseous products of the photoreduction of acetylene using GC-MS.
Figure 6B:
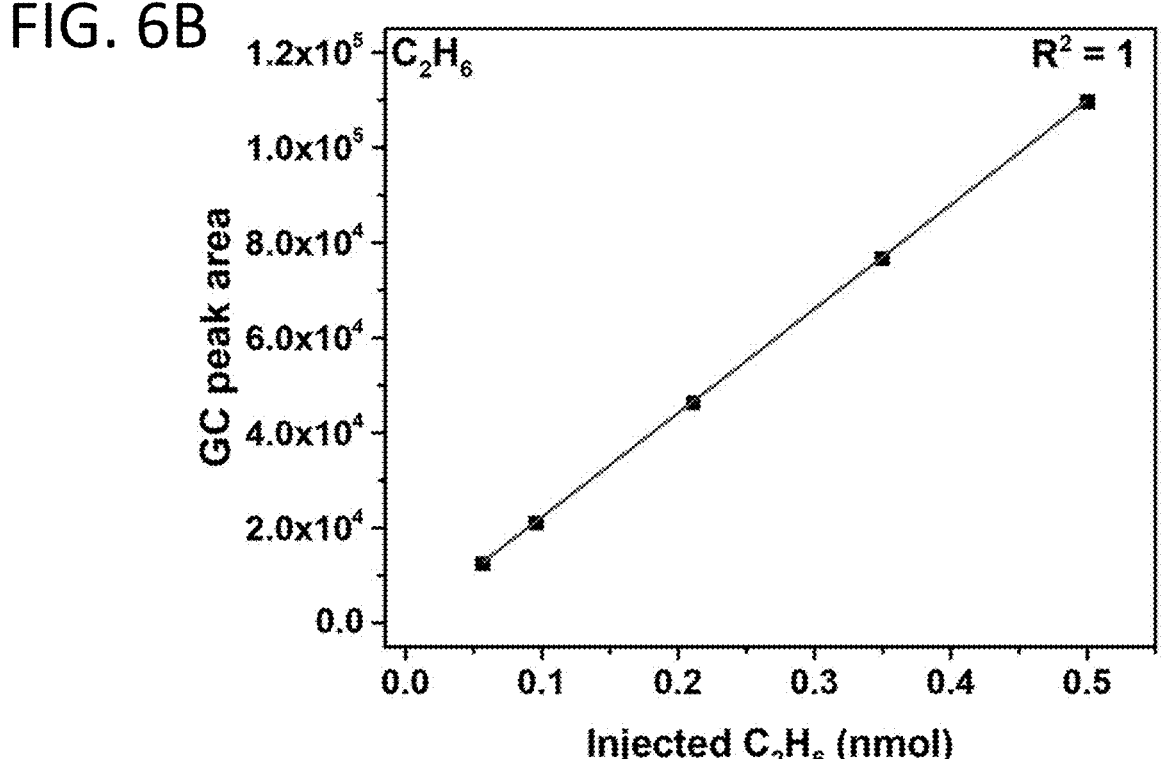

Gas chromatograms and mass spectra were collected on an Agilent Technologies 6850 Network GC system coupled with a 5975C VL MSD with Triple-Axis Detector. The GC was equipped with a HP-PLOT Q column, the inlet temperature was 250° C., the He carrier gas flow was 1.2 mL·min$^{-1}$ at a pressure of 4.30 psi. For the detection of ethylene, acetylene, and ethane the oven temperature was kept at 45° C. for 4.50 min, and then heated to 200° C. using a 30° C.·min$^{-1}$ ramp (total run time 9.67 min). For the detection of propylene, propane and propyne, the oven temperature was kept at 45° C. for 4.50 min, and then heated to 220° C. using a 30° C.·min$^{-1}$ ramp, and kept at 220° C. for 2 min (total run time 12.33 min). Headspace samples were manually injected using gas-tight Hamilton sample-lock syringes (100-250 μL). The calibration curve for C$_2$H$_4$ was collected by injecting known quantities of a gas mixture containing C$_2$H$_4$ (2 vol. % standard, He balance, Airgas). C$_2$H$_4$ is reported as "trace" in Table 1 for samples in the photoreduction of C$_2$H$_2$ (≥99.5 vol. %, Airgas) that showed ethylene below the intercept of the calibration curve (7 nmol). The calibration curve for C$_2$H$_6$ was collected by injecting known quantities of a gas standard containing C$_2$H$_6$ (100 and 4200 ppm, FIGS. 6A-6B). The selectivity for C$_2$H$_4$ is reported as >99.9% when no quantifiable C$_2$H$_6$ and H$_2$ are detected in the gas chromatograms. The amount of C$_2$H$_4$ produced per gram catalyst (mmol·g$^{-1}$ Co) and selectivity for ethylene vs. C$_2$H$_6$ and H$_2$ $$\left(S_{C2H4}^{total}\right)$$

and vs. just C$_2$H$_6$ $$\left(S_{C2H4}^{C2H2}\right)$$

for the photoreduction of C$_2$H$_2$ (≥99.5 vol. %, Airgas) were calculated as follows:

$$Amount_{C_2H_4}\left(mmol \cdot g^{-1}Co\right) =$$

$$\frac{(mol\ C_2H_4)}{\left(g\ Co-PCN-222\right)\left(wt\ \%\ Co\ in\ Co-PCN-222\right)}$$

$$S_{C_2H_4}^{total}(\%) = \frac{mol\ C_2H_4}{mol\ C_2H_4 + mol\ C_2H_6 + mol\ H_2} \times 100$$

$$S_{C_2H_4}^{C_2H_2}(\%) = \frac{mol\ C_2H_4}{mol\ C_2H_4 + mol\ C_2H_6} \times 100$$

A gas mixture containing C$_3$H$_6$ (2 vol. % standard, He balance, Airgas) and C$_3$H$_8$ (2 vol. % standard, He balance, Airgas) was injected as standard for detection of propylene and propane. Experiments were performed at least in duplicate.

Figure 7A:
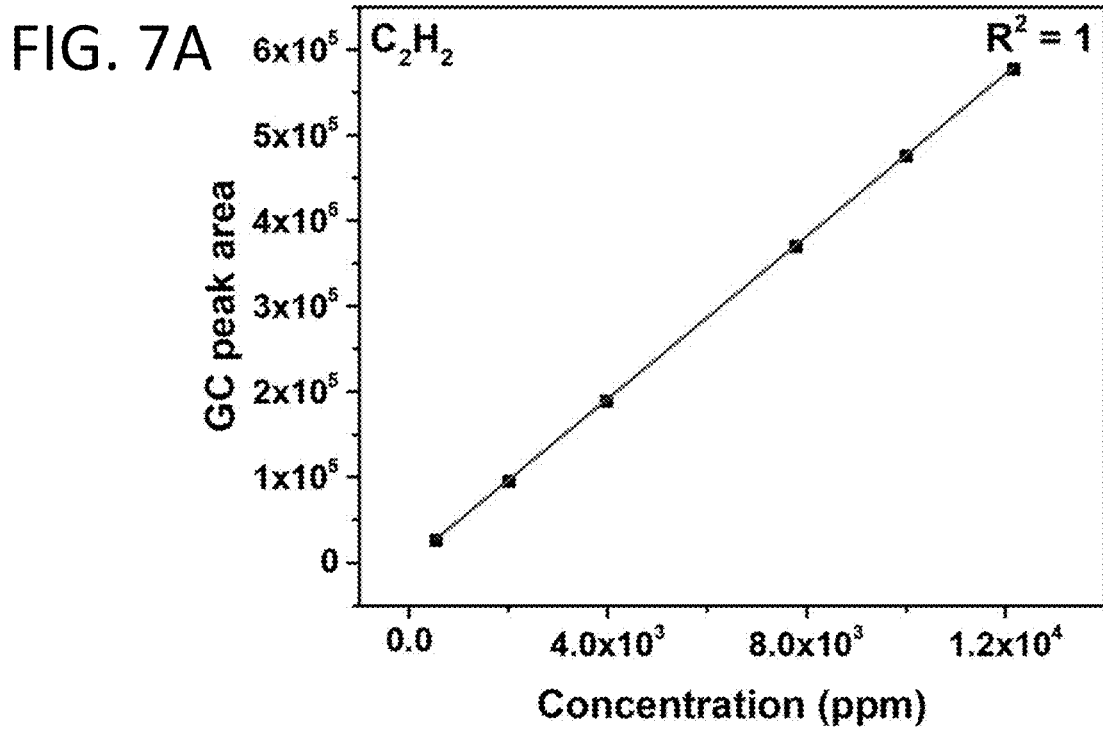
FIGS. 7A-7B show calibration curves for quantification of gaseous products of the photoreduction of the acetylene/ethylene industrial mixture using GC-FID.
Figure 7B:
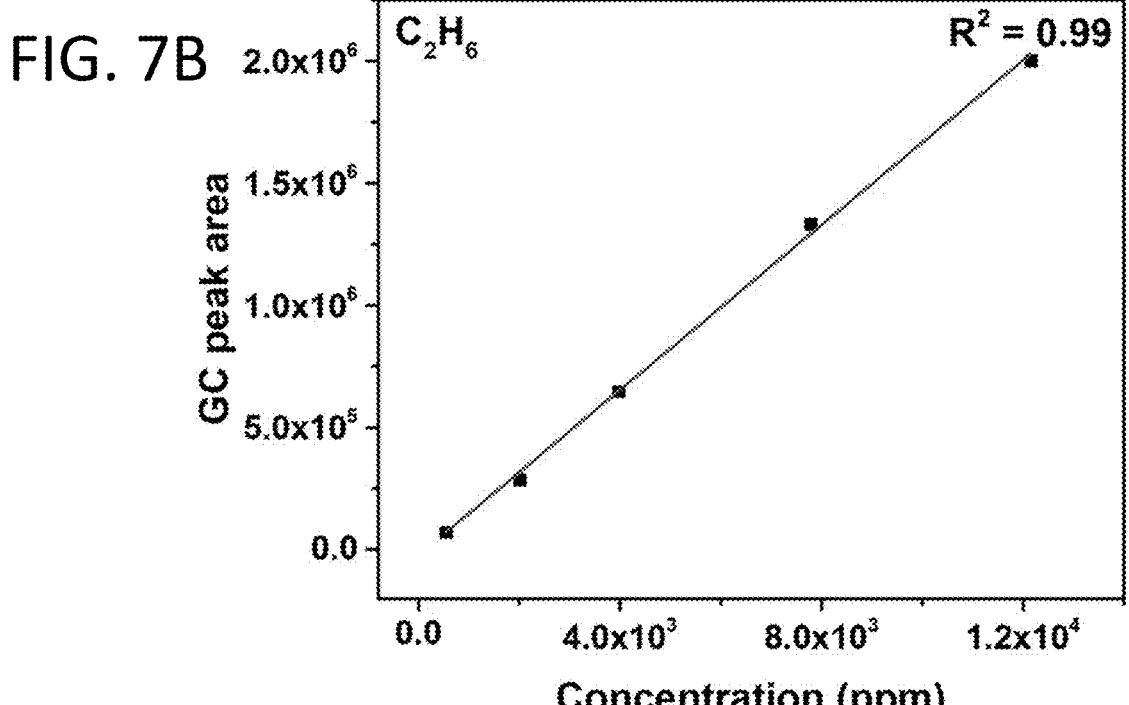

For the detection and quantification of acetylene and ethane in the photoreduction of the C$_2$H$_4$/C$_2$H$_2$ mixture (1 vol. % C$_2$H$_2$, 30 vol. % C$_2$H$_4$, He balance, Airgas) a custom-built Shimadzu GC-2014 gas chromatography system equipped with flame ionization detector (FID) was used. The column used was HayeSep T (¹⁄₁₆", 7.5 m) with an argon carrier gas flow of 7.5 mL·min$^{-1}$ min at constant pressure of 2.5-2.7 bars, and the FID detector maintained at 250° C. The oven temperature was kept at 35° C. for 9.0 min, and then heated to 85° C. using a 40° C.·min$^{-1}$ ramp, and kept at 85° C. for 4.0 min (total run time 17.0 min). Calibration curves for C$_2$H$_2$ and C$_2$H$_6$ were collected by injecting known quantities of a standard gas mixture (TOGAS 4200 ppm standard and 1% C$_2$H$_2$ in C$_2$H$_4$ and He). Experiments were performed at least in duplicate. The intercept of the calibration curves for C$_2$H$_2$ and C$_2$H$_6$ crosses zero to guarantee accuracy when the gas concentration is as low as few ppm (FIGS. 7A-7B). Injections were performed using gas-tight Hamilton syringes (10-25 μL). C$_2$H$_2$ conversion (C$_{C2H2}$) and selectivity for ethylene (S$^{C2H4}$) for the photoreduction of the C$_2$H$_4$/C$_2$H$_2$ mixture were calculated as follows:

$$C_{C_2H_2}(\%) = \frac{[C_2H_4]_{feed} - [C_2H_2]_x}{[C_2H_4]_{feed}} \times 100$$

$$S_{C_2H_4}(\%) = \frac{[C_2H_4]_{feed} - [C_2H_2]_x}{[C_2H_2]_{feed} - [C_2H_2]_x + [C_2H_6]} \times 100$$

where [C$_2$H$_2$]$_{feed}$ represents the acetylene concentration in the feed (1×10$^4$ ppm) and [C$_2$H$_2$]$_x$ and [C$_2$H$_6$] are the concentrations of acetylene and ethane in the product. The change in ethylene concentration cannot be accurately measured because of the excess of ethylene in the gas feed and therefore is not used for calculating the selectivity.

Analyses of $H_2$ gas evolved in the headspace during the photocatalysis were performed with a custom-built Shimadzu GC-2014 gas chromatography system equipped with a thermal conductivity detector. $H_2$ production was quantitatively detected using HayeSep T (1/16", 7.5 m) and MS-5A (1/16", 2.5 m) columns. The temperature was held at 100° C. for the TCD detector and 40° C. for the oven. The carrier gas was argon flowing at 8.5 mL·min$^{-1}$, at constant pressure of 3.8-4.0 bars. Injections (100 µL) were performed via an autosampler (AOC 6000) equipped with a gas-tight syringe (SGE autosampler syringe). Calibration curve for $H_2$ was collected by injecting known quantities of $H_2$ (5 vol. %, standard, Ar balance, Airgas). Experiments were performed at least in duplicate.

Absorption Spectroscopy

UV-Vis absorption spectra were recorded on a Varian Cary 5000 spectrometer. UV-Vis spectra of MOF powders were collected using an Agilent Technologies Internal DRA 2500 diffuse-reflectance UV-Vis attachment. We prepared ~1 mg/mL suspensions of each MOF in acetone and drop-cast 100-300 µL onto Platinum Line® Cover Glass microscope coverslips (22×22 #1.5). Sealable quartz cuvettes (Starna Cells with septum cap) were used for investigation of Co$^{III}$-TCPP reduction in the presence and absence of TEOA and for photostability studies of Ru(bpy)$_3{}^{2+}$, equipped with a micro stir bar and the solutions were prepared and degassed as described for the photocatalytic systems. Irradiation was performed with a 450 nm LED (140 mW·cm$^{-2}$). Acetonitrile purged with He and/or $C_2H_2$ was used as baseline.

Powder X-Ray Diffraction

PXRD measurements were collected on a STOE STADI P instrument at the Integrated Molecular Structure Education and Research Center (IMSERC) at Northwestern University. A CuKα radiation source was used. Samples were prepared by packing MOF powders into metallic flat disc transmission holders and securing the powders using Kapton tape.

Elemental Analysis

Samples were analyzed using a Thermo iCAP ICP-OES at the Quantitative Bio-element Imaging Center (QBIC) at Northwestern University. For each MOF sample, 2-3 mg (with exact mass measured using an analytical balance) were added to a 2-5 mL Biotage microwave reaction vial, along with 2 mL nitric acid (trace metal grade, Fisher) and a small stir bar. The microwave vial was then sealed, and the vessel was heated using a Biotage Initiator+ microwave reactor at 150° C. for 15 minutes until a transparent solution was obtained (Note: additional heating was required to fully digest some samples and obtain a transparent solution). 0.3 mL of the resulting solution was then diluted to a total volume of 10 mL using millipore water.

$N_2$ Sorption Isotherms $N_2$ isotherms for PCN-222 and Co-PCN-222 were collected on a Micromeritics Tristar II 3020 at 77 K. Samples were first activated under vacuum using a Micromeritics Smart VacPrep instrument at 100° C. for 12-24 h. Prior to activation, samples were thoroughly solvent exchanged by washing with acetone 3× for one hour and once overnight. Pore-size distributions were obtained using DFT calculations with a carbon slit geometry and a $N_2$ DFT model.

Scanning Electron Microscopy

Images of the materials were collected with a Hitachi SU8030 cFEG SEM at the Electron Probe Instrumentation Center (EPIC) facility, which is part of the Northwestern University Atomic and Nanoscale Characterization Experimental Center (NUANCE). Prior to imaging, the samples were deposited onto double-sided carbon tape as dry powders and coated with a 10 nm layer of osmium using an osmium coater (SPI OPC-60A).

X-Ray Photoelectron Spectroscopy

XPS measurements were carried out on a Thermo Scientific ESCALAB 250Xi instrument, which was available through the Keck-II facility, a part of the Northwestern University Atomic and Nanoscale Characterization Experimental Center (NUANCE). Samples were deposited as dry powders onto double-sided copper tape. Monochromatic X-ray source (AlKα), 500 µm spot size and a pass energy of 50 eV were used. Sample charging was prevented with a flood gun. Data analysis was performed with Thermo Avantage software, utilizing the built-in fitting routine. A Smart (constrained Shirley) background was used for all spectra. Fitting was aided and validated by comparison to published fits of CoO and $Co_3O_4$ standards. (Biesinger, M. C. et al., *Appl. Surf. Sci.* 2011, 257 (7), 2717-2730; Major, G. H. et al., *Journal of Vacuum Science & Technology A* 2020, 38 (6), 061203; Crist, B. V., Handbook of Monochromatic XPS Spectra Vol. 2 Commercially Pure Binary Oxides. XPS International LLC: www.xpsdata.com, 1999; pp. 72-78; Shard, A. G., *Journal of Vacuum Science & Technology A* 2020, 38 (4), 041201.)

Fluorescence Quenching

For the fluorescence quenching experiments, solutions of 2.5 mM Ru(bpy)$_3{}^{2+}$ in acetonitrile containing various concentrations of Co-PCN-222 or TEOA were purged for 10 minutes with He followed by 5 minutes with $C_2H_2$ (≥99.5 vol. %). The lifetimes were measured in a custom-built microscope equipped with a piezo scanner (NanoPI, Physik Instrumente), an APD detector (MicroPhoton Devices), and a photon counting board (PicoHarp300, PicoQuant) where correlation times between the excitation pulses and detected photons were recorded. The excitation pulses were synchronized from a 440 nm, 70 ps pulsed diode laser at a repetition rate of 250 kHz (Picoquant) and focused with a long working distance objective (0.7 NA, 100×, Mitutoyo), and the detected fluorescence was filtered with a 490 nm long-pass dichroic (Thorlabs) and a 495 nm long-pass filter (Thorlabs). The quenching rate constant ($k_q$) was calculated according to the Stern-Volmer equation:

$$\frac{\tau_0}{\tau} = 1 + k_q \times \tau_0 \times [Q]$$

where $\tau_0$ and $\tau$ are the lifetime of Ru(bpy)$_3{}^{2+}$ in absence ($\tau_0$=966 ns) and in presence of quencher and [Q] is the molar concentration of the quencher ([TEOA]=0.125-2.0 M, [Co] =0.2-2 mM). The measured bimolecular rate constants are $k_q{}^{TEOA}$=3.57×10$^4$ M$^{-1}$·s$^{-1}$ and $k_q{}^{Co}$=1.05×10$^8$ M$^{-1}$·s$^{-1}$, which correspond to unimolecular rate constants $k_q$[TEOA] =4.47×10$^4$ s$^{-1}$ and $k_q$[Co]=3.34×10$^4$ s$^{-1}$ for the concentrations of these species ([TEOA]=1.25 M, [Co]=0.32 mM) used in our catalytic reaction mixtures.

Measurement of Quantum Yields

The quantum yield of a photochemical process is calculated as the number of defined events occurring per photon absorbed by the system at a specific wavelength. The $\Phi_{C2H4}(\%)$ was therefore calculated according to the following equation:

$$\Phi_{C_2H_4}(\%) = \frac{\text{number of } C_2H_4 \text{ molecules} \times 2}{\text{number of photons absorbed}} \times 100$$

To calculate the fraction of photons absorbed, we determined the amount of absorbed light at the beginning of the photocatalytic experiments from (at least) three independent readings of the measured power at the top of the reaction vessel (an Optical Power Meter PM100D with Optical Sensor S120VC from Thorlabs was used). The reaction vessel contained a 2.0 mL solution of 1.25 M TEOA in acetonitrile to account for the reflection loss at the glass/air interface. The number of photons absorbed was calculated taking the photon wavelength equal to 450 nm, an incident light power of 140 $mW \cdot cm^{-2}$ and considering an illuminated area of 1.767 $cm^2$. Under our conditions, 2.0 mL of a solution containing 2.5 mM $Ru(bpy)_3^{2+}$, 1.25 M TEOA and 0.8 mg Co-PCN-222 absorbed 98% of incident photons. The number of molecules of $C_2H_4$ were determined from the moles of $C_2H_4$ in the sample headspace (obtained by GC-MS measurements) from three independent experiments (at 4 h of irradiation). The $\Phi C_2H_4$ was calculated to be 0.02%.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for photocatalytic reduction of an alkyne to an alkene, the method comprising:

exposing the alkyne to a solution comprising: a metal-organic framework comprising inorganic metal ions or clusters connected by polytopic organic linkers, the polytopic organic linkers comprising cobalt-porphyrin groups; a photosensitizer; and a sacrificial donor; and irradiating the photosensitizer with visible radiation to induce the photocatalytic reduction of the alkyne to the alkene.

2. The method of claim 1, wherein the alkyne comprises acetylene, propyne, or a mixture thereof.

3. The method of claim 2, wherein the solution is simultaneously exposed to the acetylene and ethylene and the acetylene is selectively reduced relative to the ethylene.

4. The method of claim 2, wherein the metal-organic framework is Co-(Zr)PCN-222.

5. The method of claim 2, wherein the photosensitizer is a rubidium polypyridine complex.

6. The method of claim 5, wherein the rubidium polypyridine complex comprises tris (bipyridine) ruthenium (II).

7. The method of claim 2, wherein the sacrificial donor is a tertiary aliphatic amine.

8. The method of claim 7, wherein the tertiary aliphatic amine is triethanolamine.

9. The method of claim 2, wherein irradiating the photosensitizer with visible radiation comprises exposing the photosensitizer and the solution to solar radiation.

10. The method of claim 3, wherein the photosensitizer is a rubidium polypyridine complex and the sacrificial donor is a tertiary aliphatic amine.

11. The method of claim 10, wherein the rubidium polypyridine complex comprises tris(bipyridine)ruthenium(II) and the tertiary aliphatic amine is triethanolamine.

12. The method of claim 11, wherein the solution is simultaneously exposed to the acetylene and ethylene and at least 90 mol. % of the acetylene is reduced with a selectivity of acetylene reduction over ethylene reduction of at least 90%.

13. The method of claim 11, wherein the solution is simultaneously exposed to the acetylene and ethylene and the cobalt-porphyrin groups catalyze the reduction of at least 99 mol. % of the acetylene with a selectivity of acetylene reduction over ethylene reduction of at least 99%.

14. The method of claim 13, wherein the metal-organic framework is Co-(Zr)PCN-222.

15. The method of claim 1, wherein the reduction of the alkyne is carried out at a temperature in the range from 20° C. to 25° C.

16. The method of claim 1, wherein the metal-organic framework is Co-(Zr)PCN-222.

17. The method of claim 1, wherein the photosensitizer is a rubidium polypyridine complex.

18. The method of claim 17, wherein the rubidium polypyridine complex comprises tris(bipyridine)ruthenium(II).

19. The method of claim 1, wherein the sacrificial donor is a tertiary aliphatic amine.

20. The method of claim 19, wherein the tertiary aliphatic amine is triethanolamine.

\* \* \* \* \*